(12) United States Patent
Lobl et al.

(10) Patent No.: US 7,803,148 B2
(45) Date of Patent: Sep. 28, 2010

(54) FLOW-INDUCED DELIVERY FROM A DRUG MASS

(75) Inventors: Thomas J. Lobl, Valencia, CA (US);
Anna Imola Nagy, Valencia, CA (US);
Jacob E. Pananen, Pasadena, CA (US);
John V. Schloss, Saugus, CA (US)

(73) Assignee: NeuroSystec Corporation, Valencia, CA (US)

( * ) Notice: Subject to any disclaimer, the term of this patent is extended or adjusted under 35 U.S.C. 154(b) by 0 days.

(21) Appl. No.: 11/759,387

(22) Filed: Jun. 7, 2007

(65) Prior Publication Data

US 2007/0287984 A1 Dec. 13, 2007

Related U.S. Application Data

(60) Provisional application No. 60/804,394, filed on Jun. 9, 2006.

(51) Int. Cl.
*A61M 5/32* (2006.01)
*A61M 37/00* (2006.01)
*A61K 9/22* (2006.01)
*A61K 9/14* (2006.01)
*A61F 13/00* (2006.01)
*A61F 2/00* (2006.01)

(52) U.S. Cl. ............... 604/416; 604/131; 604/288.01; 604/288.04; 604/891.1; 604/892.1; 424/422; 424/423; 424/427; 424/489

(58) Field of Classification Search ............... 424/422, 424/423, 427, 489; 604/123, 131, 288.01, 604/288.04, 890.1, 891.1, 892.1; 623/5.11
See application file for complete search history.

(56) References Cited

U.S. PATENT DOCUMENTS

| | | | |
|---|---|---|---|
| 3,850,161 | A | 11/1974 | Liss |
| 3,881,495 | A | 5/1975 | Pannozzo et al. |
| 4,034,756 | A | 7/1977 | Higuchi et al. |
| 4,232,679 | A | 11/1980 | Schulman |
| 4,360,019 | A | 11/1982 | Portner et al. |
| 4,408,608 | A | 10/1983 | Daly et al. |
| 4,481,950 | A | 11/1984 | Duggan |
| 4,484,921 | A * | 11/1984 | Swanson et al. ............ 424/427 |

(Continued)

FOREIGN PATENT DOCUMENTS

EP 343910 11/1989

(Continued)

OTHER PUBLICATIONS

Gaviria, M. et al. Brain Research. vol. 874, Iss. 2, Aug. 25, 2000, p. 200-209. "Neuroprotective Effects of a Novel NMDA Antagonist, Gacyclidine, After Experimental Contusive Spinal Cord Injury in Adult Rats."*

(Continued)

*Primary Examiner*—Tatyana Zalukaeva
*Assistant Examiner*—Adam Marcetich
(74) *Attorney, Agent, or Firm*—Banner & Witcoff, Ltd.

(57) ABSTRACT

Drug solutions (or other combinations of vehicle with entrained drug) are prepared by removing drug from one or more masses of a solid form of the drug. The solid form of the drug may be sparingly soluble or insoluble in water. Examples of devices for holding solid drug and facilitating delivery of such drug to targeted regions are also described.

20 Claims, 18 Drawing Sheets

U.S. PATENT DOCUMENTS

| | | | |
|---|---|---|---|
| 4,487,603 A | 12/1984 | Harris | |
| 4,511,355 A | 4/1985 | Franetzki et al. | |
| 4,590,946 A | 5/1986 | Loeb | |
| 4,608,985 A | 9/1986 | Crish et al. | |
| 4,628,942 A | 12/1986 | Sweeney et al. | |
| 4,639,244 A * | 1/1987 | Rizk et al. | 604/19 |
| 4,649,936 A | 3/1987 | Ungar et al. | |
| 4,692,147 A | 9/1987 | Duggan | |
| 4,702,254 A | 10/1987 | Zabara | |
| 4,725,852 A | 2/1988 | Gamblin et al. | |
| 4,756,710 A * | 7/1988 | Bondi et al. | 424/449 |
| 4,819,647 A | 4/1989 | Byers et al. | |
| 4,929,236 A | 5/1990 | Sampson | |
| 4,944,659 A | 7/1990 | Labbe et al. | |
| 5,041,107 A * | 8/1991 | Heil, Jr. | 604/891.1 |
| 5,188,104 A | 2/1993 | Wernicke et al. | |
| 5,207,640 A * | 5/1993 | Hattler | 604/28 |
| 5,215,086 A | 6/1993 | Terry, Jr. et al. | |
| 5,299,569 A | 4/1994 | Wernicke et al. | |
| 5,305,445 A | 4/1994 | Nishikawa | |
| 5,305,745 A | 4/1994 | Zacouto | |
| 5,314,458 A | 5/1994 | Najafi et al. | |
| 5,330,515 A | 7/1994 | Rutecki et al. | |
| 5,354,279 A | 10/1994 | Hofling | |
| 5,358,514 A | 10/1994 | Schulman et al. | |
| 5,421,818 A | 6/1995 | Arenberg | |
| 3,894,538 A | 7/1995 | Richter | |
| 5,441,481 A * | 8/1995 | Mishra et al. | 604/29 |
| 5,468,253 A | 11/1995 | Bezwada | |
| 5,474,529 A | 12/1995 | Arenberg | |
| 5,476,446 A | 12/1995 | Arenburg | |
| 5,538,735 A * | 7/1996 | Ahn | 424/443 |
| 5,545,152 A | 8/1996 | Funderburk et al. | |
| 5,563,140 A | 10/1996 | Ehrenberger et al. | |
| 5,643,207 A | 7/1997 | Rise | |
| 5,690,652 A | 11/1997 | Wurster et al. | |
| 5,700,282 A | 12/1997 | Zabara | |
| 5,707,361 A | 1/1998 | Slettenmark | |
| 5,716,318 A | 2/1998 | Manning | |
| 5,728,396 A | 3/1998 | Peery et al. | |
| 5,752,979 A | 5/1998 | Benabid | |
| 5,755,750 A | 5/1998 | Petruska et al. | |
| 5,836,935 A | 11/1998 | Ashton et al. | |
| 5,849,015 A | 12/1998 | Haywood et al. | |
| 5,863,927 A | 1/1999 | Smith et al. | |
| 5,865,789 A * | 2/1999 | Hattler | 604/26 |
| 5,895,372 A | 4/1999 | Zenner et al. | |
| 5,895,416 A | 4/1999 | Barreras et al. | |
| 5,945,052 A | 8/1999 | Schryver et al. | |
| 5,971,953 A * | 10/1999 | Bachynsky | 604/90 |
| 5,980,928 A | 11/1999 | Terry | |
| 5,985,305 A | 11/1999 | Peery et al. | |
| 5,995,868 A | 11/1999 | Dorfmeister et al. | |
| 6,013,051 A | 1/2000 | Nelson | |
| 6,045,528 A | 4/2000 | Arenberg et al. | |
| 6,066,652 A | 5/2000 | Zenner et al. | |
| 6,067,474 A | 5/2000 | Schulman et al. | |
| 6,104,956 A | 8/2000 | Naritoku et al. | |
| 6,112,116 A | 8/2000 | Fichell et al. | |
| 6,129,753 A | 10/2000 | Kuzma | |
| 6,178,349 B1 | 1/2001 | Kieval | |
| 6,181,969 B1 | 1/2001 | Gord | |
| 6,205,359 B1 | 3/2001 | Boveja | |
| 6,219,580 B1 | 4/2001 | Faltys et al. | |
| 6,266,564 B1 | 7/2001 | Hill et al. | |
| 6,309,410 B1 | 10/2001 | Kuzma et al. | |
| 6,341,236 B1 | 1/2002 | Osorio et al. | |
| 6,377,849 B1 | 4/2002 | Lenarz et al. | |
| 6,393,325 B1 | 5/2002 | Mann et al. | |
| 6,409,698 B1 * | 6/2002 | Robinson et al. | 604/19 |
| 6,436,405 B1 | 8/2002 | Bakaletz et al. | |
| 6,440,102 B1 | 8/2002 | Arenberg et al. | |
| 6,450,984 B1 | 9/2002 | Lynch et al. | |
| 6,458,118 B1 | 10/2002 | Lent et al. | |
| 6,464,687 B1 * | 10/2002 | Ishikawa et al. | 604/891.1 |
| 6,526,318 B1 | 2/2003 | Ansarinia | |
| 6,560,490 B2 | 5/2003 | Grill et al. | |
| 6,568,910 B1 * | 5/2003 | Parce | 417/40 |
| 6,585,703 B1 | 7/2003 | Kassel et al. | |
| 6,596,752 B1 | 7/2003 | Lobl et al. | |
| 6,597,954 B1 | 7/2003 | Pless et al. | |
| 6,613,026 B1 | 9/2003 | Palasis et al. | |
| 6,627,246 B2 | 9/2003 | Mehta et al. | |
| 6,648,873 B2 | 11/2003 | Arenberg et al. | |
| 6,656,172 B1 | 12/2003 | Hildebrand | |
| 6,670,321 B1 | 12/2003 | Adamis | |
| 6,685,697 B1 | 2/2004 | Arenberg et al. | |
| 6,692,481 B2 | 2/2004 | Guerrero | |
| 6,712,753 B2 | 3/2004 | Manne | |
| 6,718,209 B2 | 4/2004 | Williamson et al. | |
| 6,726,678 B1 | 4/2004 | Nelson et al. | |
| 6,743,204 B2 | 6/2004 | Christenson et al. | |
| 6,766,817 B2 | 7/2004 | da Silva | |
| 6,782,292 B2 | 8/2004 | Whitehurst | |
| 6,796,957 B2 | 9/2004 | Carpenter et al. | |
| 6,826,428 B1 | 11/2004 | Chen et al. | |
| 6,827,559 B2 | 12/2004 | Peters et al. | |
| 6,858,220 B2 | 2/2005 | Greenberg et al. | |
| 6,894,456 B2 | 5/2005 | Tsukamoto et al. | |
| 6,907,295 B2 | 6/2005 | Gross et al. | |
| 6,918,404 B2 | 7/2005 | Dias da Silva | |
| 6,928,320 B2 | 8/2005 | King | |
| 6,962,580 B2 | 11/2005 | Adams et al. | |
| 7,060,284 B1 | 6/2006 | Kaumaya et al. | |
| 7,066,586 B2 | 6/2006 | da Silva | |
| 7,079,903 B2 | 7/2006 | O'Brien | |
| 7,181,287 B2 | 2/2007 | Greenberg | |
| 7,200,504 B1 | 4/2007 | Fister | |
| 7,203,548 B2 | 4/2007 | Whitehurst et al. | |
| 7,242,985 B1 | 7/2007 | Fridman et al. | |
| 7,272,449 B2 | 9/2007 | Dadd et al. | |
| 7,277,760 B1 | 10/2007 | Litvak et al. | |
| 7,285,255 B2 | 10/2007 | Kadlec et al. | |
| 7,292,890 B2 | 11/2007 | Whitehurst et al. | |
| 7,297,130 B2 | 11/2007 | Bergheim et al. | |
| 7,308,303 B2 | 12/2007 | Whitehurst et al. | |
| 7,347,854 B2 | 3/2008 | Shelton et al. | |
| 2001/0003799 A1 | 6/2001 | Boveja | |
| 2001/0041870 A1 * | 11/2001 | Gillis et al. | 604/164.09 |
| 2002/0016615 A1 | 2/2002 | Dev et al. | |
| 2002/0022873 A1 | 2/2002 | Erickson et al. | |
| 2002/0095133 A1 | 7/2002 | Gillis et al. | |
| 2002/0182186 A1 | 12/2002 | Loeb | |
| 2002/0183722 A1 | 12/2002 | Harper et al. | |
| 2002/0188282 A1 * | 12/2002 | Greenberg | 604/890.1 |
| 2003/0083698 A1 | 5/2003 | Whitehurst et al. | |
| 2003/0097121 A1 | 5/2003 | Jolly et al. | |
| 2003/0114830 A1 * | 6/2003 | Guerrero | 604/521 |
| 2003/0171738 A1 * | 9/2003 | Konieczynski et al. | 604/891.1 |
| 2003/0203890 A1 | 10/2003 | Steiner et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0043052 A1 | 3/2004 | Hunter et al. | |
| 2004/0044389 A1 | 3/2004 | Crawford | |
| 2004/0049175 A1 | 3/2004 | Speck et al. | |
| 2004/0091995 A1 | 5/2004 | Schlom et al. | |
| 2004/0105888 A1 * | 6/2004 | Pratt et al. | 424/486 |
| 2004/0141925 A1 | 7/2004 | Bosch et al. | |
| 2004/0156858 A1 | 8/2004 | Franzusoff et al. | |
| 2004/0172005 A1 | 9/2004 | Arenberg et al. | |
| 2004/0172089 A1 | 9/2004 | Whitehurst et al. | |
| 2004/0209836 A1 | 10/2004 | Spencer et al. | |

| | | | |
|---|---|---|---|
| 2004/0223949 A1 | 11/2004 | Astsaturov et al. | |
| 2004/0243182 A1 | 12/2004 | Cohen et al. | |
| 2004/0267238 A1 | 12/2004 | Haarala et al. | |
| 2005/0013812 A1 | 1/2005 | Dow et al. | |
| 2005/0049578 A1 | 3/2005 | Tu et al. | |
| 2005/0085778 A1 | 4/2005 | Parks | |
| 2005/0101878 A1 | 5/2005 | Daly et al. | |
| 2005/0119636 A1* | 6/2005 | Haffner et al. | 604/500 |
| 2005/0130904 A1 | 6/2005 | Schloss | |
| 2005/0130920 A1 | 6/2005 | Simard et al. | |
| 2005/0137651 A1 | 6/2005 | Litvak et al. | |
| 2005/0184004 A1 | 8/2005 | Rodgers et al. | |
| 2005/0233964 A1 | 10/2005 | Kaumaya et al. | |
| 2005/0238506 A1 | 10/2005 | Mescher et al. | |
| 2005/0245906 A1* | 11/2005 | Makower et al. | 604/891.1 |
| 2005/0245971 A1 | 11/2005 | Brockway et al. | |
| 2005/0256560 A1 | 11/2005 | Lenarz | |
| 2005/0267422 A1 | 12/2005 | Kriesel | |
| 2005/0277912 A1 | 12/2005 | John | |
| 2006/0009805 A1* | 1/2006 | Jensen et al. | 607/2 |
| 2006/0030837 A1 | 2/2006 | McKenna et al. | |
| 2006/0041182 A1* | 2/2006 | Forbes et al. | 600/12 |
| 2006/0047270 A1 | 3/2006 | Shelton | |
| 2006/0063802 A1 | 3/2006 | Guitton et al. | |
| 2006/0100672 A1 | 5/2006 | Litvak | |
| 2006/0106446 A1 | 5/2006 | Fridman et al. | |
| 2006/0177495 A1 | 8/2006 | Allen et al. | |
| 2006/0205789 A1 | 9/2006 | Lobl et al. | |
| 2006/0229688 A1 | 10/2006 | McClure et al. | |
| 2006/0264897 A1 | 11/2006 | Lobl et al. | |
| 2007/0005308 A1 | 1/2007 | Lee et al. | |
| 2007/0021800 A1 | 1/2007 | Whitehurst et al. | |
| 2007/0088335 A1 | 4/2007 | Jolly | |
| 2007/0123938 A1 | 5/2007 | Haller et al. | |
| 2007/0255237 A1 | 11/2007 | Lobl et al. | |
| 2007/0260292 A1 | 11/2007 | Faltys et al. | |
| 2008/0009836 A1 | 1/2008 | Fiering et al. | |
| 2008/0033520 A1 | 2/2008 | Jolly | |
| 2008/0065002 A1 | 3/2008 | Lobl et al. | |
| 2008/0145439 A1 | 6/2008 | Lobl et al. | |

FOREIGN PATENT DOCUMENTS

| | | |
|---|---|---|
| WO | 9727840 | 8/1997 |
| WO | 9917819 | 4/1999 |
| WO | 0004854 | 2/2000 |
| WO | 2003072193 | 9/2003 |
| WO | 03099351 | 12/2003 |
| WO | 2004022069 | 3/2004 |
| WO | 2005072793 | 8/2005 |
| WO | 2006053101 | 5/2006 |
| WO | 2007030496 | 3/2007 |

OTHER PUBLICATIONS

András Hermann, et al., "Interference of S-Nitrosoglutathione with the Binding of Ligands to Ionotropic Glutamate Receptors in Pig Cerebral Cortical Synaptic Membranes," Neurochemical Research, vol. 25, No. 8, 2000, pp. 1119-1124.

C.P. Taylor, "Mechanisms of Action of Gabapentin", Rev Neurol (Paris), 1997; 153 Suppl. 1:S39-45.

Piotr Popik, et al., "The Putative Anti-Addictive Drug Ibogaine is a Competitive Inhibitor of [3H]MK-801 Binding to the NMDA Receptor Complex", Psychoparmacology (1994) 114: 672-674.

Mark J. Ginski, et al., "Sensitive and Rapid Behavioral Differentiation of N-methyl-D-aspartate Receptor Antagonists", Psychopharmacology (1994) 114:573-582.

Karin Agerman, et al., "Neurotrophins, NMDA Receptors, and Nitric Oxide in Development and Protection of the Auditory System", Annals New York Academy of Sciences, Nov. 28, 1999, 884:131-142.

Anthony S. Basile, et al., "N-Methyl-D-aspartate Antagonists Limit Aminoglycoside Antiobiotic-Induced Hearing Loss", Nature Medicine, vol. 2, No. 12, Dec. 1996, pp. 1338-1343.

Zhiqiang Chen, et al., "Acute Treatment of Noise Trauma with Local Caroverine Application in the Guinea Pig", Acta Otolaryngol, Oct. 2003; 123(8):905-909.

Zhiqiang Chen, et al., "Protection of Auditory Function Against Noise Trauma with Local Caroverine Administration in Guinea Pigs", Hearing Research 197 (1-2), 2004, pp. 131-136.

E. Costa, "From GABAA Receptor Diversity Emerges a Unified Vision of GABAergic Inhibition", Annu. Rev. Pharmacol. Toxicol. 1998, 38:321-50.

Maoli Duan, et al., "Complementary Roles of Neurotrophin 3 and a N-methyl-D-aspartate Antagonist in the Protection of noise and Aminoglycoside-induced Ototoxicity", PNAS, Jun. 20, 2000, vol. 97, No. 13, pp. 7597-7602.

Sophie Feldblum, et al., "Efficacy of a New Neuroprotective Agent, Gacyclidine, in a Model of Rat Spinal Cord Injury", Journal of Neurotrauma, vol. 17, No. 11, 2000, pp. 1079-1093.

Frauke Fischer, et al., "List of Drugs in Development for Neurodegenerative Diseases", Neurodegenerative Dis 2004; 1:50-70.

Ruggero Galici, et al., "Tolerance to and Dependence on Alprazolam are Due to Changes in GABAA Receptor Function and are Independent of Exposure to Experimental Set-up", Restorative Neurology and Neuroscience 12 (1998); pp. 233-237.

Michael J. Gallagher, et al., "Interactions Between Ifenprodil and the NR2B Subunit of the N-Methyl-D-aspartate Receptor", The Journal of Biological Chemistry, vol. 271, No. 16, Issue of Apr. 19, 1996, pp. 9603-9611.

Matthieu J. Guitton, et al., "New Pharmacological Strategies to Restore Hearing and treat Tinnitus", Acta Otolaryngol, 2004; 124: 411-415.

Greta Ann Herin, et al., "The Neuroprotective Agent Ebselen Modifies NMDA Receptor Function via the Redox Modulatory Site", Journal fo neurochemistry, 2001, 78, 1307-1314.

B.K. K Kohl, et al. "The NMDA Receptor Complex: A Promising Target for Novel Antiepileptic Strategies", Current Medicinal Chemistry, Sep. 2001, 8, 1275-1289.

Richard D. Kopke, et al., "Enhancing Intrinsic Cochlear Stress Defenses to Reduce Noise-Induced Hearing Loss", The Laryngoscope 112: Sep. 2002, pp. 1515-1532.

David B. Moody, "Animal Models of Tinnitus", Tinnitus: Theory and Management, Chapter 7, pp. 80-95 (2004).

Alan L. Mueller, et al., "NPS 1506, A Novel NMDA Receptor Antagonist and Neuroprotectant, Review of Preclinical and Clinical Studies", Annals New York Academy of Sciences, 1999; 890:450-457.

M. Nankai, et al., "NMDA Receptor Subtype Selectivity: Eliprodil, Polyamine Spider Toxins, Dextromethorphan, and Desipramine Selectively Block NMDA-Evoked Striatal Acetylcholine but Not Spermidine Release", Journal of Neurochemistry, May 1995; 64(5): pp. 2043-2048.

Nagendra S. Ningaraj, et al., "S-Methyl-N, N-Diethylthiocarbamate Sulfoxide Elicits Neuroprotective Effect against N-Methyl-D-Aspartate Receptor-Mediated Neurotoxicity", Journal of Biomedical Science 2001; 8:104-113.

Dominik Oliver, et al., "Memantine Inhibits Efferent Cholinergic Transmission in the Cochlea by Blocking Nicotinic Acetylcholine Receptors of Outer Hair Cells", Molecular Pharmacology, vol. 60, No. 1, Jul. 2001; 60(1):183-189.

Wojciech Danysz, et al., "Glycine and N-Methyl-D-Aspartate Receptors: Physiological Significance and Possible Therapeutic Applications", Pharmacological Reviews, vol. 50, No. 4, pp. 597-664 (1998).

Gene C. Palmer, "Neuroprotection by NMDA Receptor Antagonists in a Variety of Neuropathologies", Current Drug Targets, Sep. 2001, 2(3):241-71.

Rémy Pujol, et al., "Excitotoxicity, Synaptic Repair, and Functional Recovery in the Mammalian Cochlea: A Review of Recent Findings", Annals of the New York Academy of Sciences, 1999, 884: 249-254.

Masahiro Sugimoto, et al., Local Anaesthetics Have Different Mechanisms and Sites of Action at the Recombinant N-methyl-D-aspartate (NMDA) Receptors), British Journal of Pharmacology (2003) 138, 876-882.

Stephen M. Stahl, "Anticonvulsants and the Relief of Chronic Pain: Pregabalin and Gabapentin as alpha-2-delta Ligands at Voltage-Gated Calcium Channels", J. Clin. Psychiatry 65:5, May 2004, pp. 596-597.

Li-Ming Zhou, et al., "Synthetic Analogues of Conantokin-G: NMDA Antagonists Acting Through a Novel Polyamine-Coupled Site", Journal of Neurochemistry, Feb. 1996, 66(2): 620-8.

David R. Lynch, et al., "Pharmacological Characterization of Interactions of RO 25/6981 with the NR2B ( 2) Subunit", European Journal of Pharmacology 416 (2001): 185-195.

David R. Lynch, et al., "Inhibition of N-Methyl-D-Aspartate Receptors by Haloperidol: Developmental and Pharmacological Characterization in Native and Recombinant Receptors1", The Journal of Pharmacology and Experimental Therapeutics, vol. 279, No. 1, Oct. 1996:154-61.

Matthieu J. Guitton, et al., "New Pharmacological Strategies to Restore Hearing and Treat Tinnitus", Acta Otolaryngol 2004; 124:411-415.

Barbara A. Goldstein, et al., "Tinnitus Outcome Profile and Tinnitus Control", International Tinnitus Journal, vol. 9, No. 1, 2003: 26-31.

Doris-Maria Denk, et al., "Caroverine in Tinnitus Treatment", Acta Otolaryngol (Stockh) 1997; 117:825-830.

M.B. Hesselink, et al., "Modifications of the Behavioral Profile of Non-Competitive NMDA Receptor Antagonists, memantine, amantadine and (+)MK-801 after Chronic Administration", Behavioural Pharmacology 1999; 10:85-98.

Wojciech Danysz, et al., "Neuroprotective Potential of Ionotropic glutamate Receptor Antagonists", Neurotoxicity Research, 2002, vol. 4(2), pp. 119-126.

T. Oma Hester, et al., "Cyclandelate in the Management of Tinnitus: A Randomized, Placebo-Controlled Study", Otolaryngol Head neck Surg., Mar. 1998, 118(3, Pt. 1): 329-332.

Jan H. Hulshof, et al., "The Value of Tocainide in the Treatment of Tinnitus, A Double-Blind Controlled Study", Arch Otorhinolaryngol (1985) 241:279-283.

Th. Lenarz, "Treatment of Tinnitus with Lidocaine and Tocainide", Scand. Audiol. Suppl., 1986: 26:49-51.

Leif Nordang, et al., "Glutamate is the Afferent Neurotransmitter in the Human Cochlea", Acta Otolaryngol 2000; 120:359-362.

Elmar Oestreicher, et al., "Memantine Suppresses theGlutamatergic Neurotransmission of Mammalian Inner Hair Cells", ORL J. Otorhinolaryngol Relat. Spec., Jan.-Feb. 1998; 60(1):18-21.

Elmar Oestreicher, et al., "New Approaches for Inner Ear Therapy with Glutamate Antagonists", Acta Otolaryngol, Mar. 1999; 119(2):174-178.

Elmar Oestreicher, et al., "Different Action of Memantine and Caroverine on Glutamatergic Transmission in the Mammalian Cochlea", Adv. Otorhinolaryngol, 2002; 59:18-25.

E. Perucca, et al., A Controlled Study of the Suppression of Tinnitus by Lidocaine Infusion: (Relationship of Therapeutic Effect with Serum Lidocaine Levels); The Journal of Laryngology and Otology, Jul. 1985, vol. 99, pp. 657-661.

Michael D. Seidman, et al., "Pharmacologic Manipulation of the Labyrinth with Novel and Traditional Agents Delivered to the Inner Ear", ENT-Ear, Nose & Throat Journal, Apr. 2003; 82(4); 276-280, 282-283, 287-288.

Wojciech Danysz, et al., "Glutamate Antagonists Have Different Effects on Spontaneous Locomotor Activity in Rats", Pharmacology Biochemistry and Behavior, 1994, vol. 48, No. 1, pp. 111-118.

Chrysanthy Ikonomidou, et al., "Why did NMDA Receptor Antagonists Fail Clinical Trials for Stroke and Traumatic Brain Injury?", The Lancet neurology, vol. 1(6), Oct. 2002: 383-386.

T. Lenarz, et al., "Tinnitus Therapy with Liodcaine and Tocainide", Laryngol Rhinol. Otol (Stuttg.); Dec. 1985, 64 (12):604-608 (with English Abstract).

K. Ogita, et al., "Nitric Oxide-Independent Inhibition by Sodium Nitroprusside of the Native N-methyl-D-aspartate Recognition Domain in a Manner Different from that by Potassium Ferrocyanide", Neurochem. Int. 33 (1998):1-9.

Steven L. Peterson, et al., "Differential Neuroprotective Effects of the NMDA Receptor-Associated Glycine Site Partial Agonists 1-Aminocyclopropanecarboxylic Acid (ACPC) and D-Cycloserine in Lithium-Pilocarpine Status Epilepticus", NeuroToxicology 25 (2004):835-847.

Margaret A. Petty, et al., "ACEA 1021: Flip or Flop?", CNS Drive Reviews, vol. 10, No. 4, pp. 337-348 (2004).

Jacob B. Schwarz, et al., "Novel Cyclopropyl B-Amino Acid Analogues of Pregabalin and gabapentin that Target the alpha-2-delta Protein", J. Med. Chem. 2005, 48, pp. 2026-3035.

Stanislaw J. Czuczwar, et al., "The New Generation of GABA Enhancers, Potential in the Treatment of Epilepsy", CNS Drugs, 2001; 15(5):339-350.

David J. Hewitt, et al., "The Use of NMDA-Receptor Antagonists in the Treatment of Chronic Pain", The Clinical Journal ofPain, Jun. 2000; 16(2 Suppl.):S73-79.

Sveta Mayer, et al., "Acamprosate, MK-801, and Ifenprodil Inhibit Neurotoxicity and Calcium Entry Induced by Ethanol Withdrawal in Organotypic Slice Cultures from Neonatal Rat Hippocampus", Alcohol Clin. Exp. Res., Oct. 2002; 26 (10):1468-78.

Zhang-Lin Zhou, et al., "4-Hydroxy-1-[2-(4-hydroxyphenoxy)ethyl]-4-(4-methylbenzyl)piperidine: A Novel, Potent, and Selective NR1/2B NMDA Receptor Antagonist", J. Med. Chem. 1999, 42, 2993-3000.

Richard K. Gordon, et al., "The NMDA Receptor Ion Channel: a Site for Binding of Huperzine A", Journal of Applied Toxicology, 2001;21:S47-S51.

C.G. Parsons, et al., Comparison of the Potency, Kinetics and Voltage-Dependency of a Series of UnCompetitive NMDA Receptor Antagonists In Vitro with Anticonvulsive and Motor Impairment Activity In Vitro, Neuropharmacology, 1995; vol. 34, No. 10, pp. 1239-1258.

U.S. Appl. No. 60/665,171, filed Mar. 24, 2005.

Naveen K. Dakappagari, et al., "A Chimeric Multi-Human Epidermal Growth Factor Receptor-2 B Cell Epitope Peptide Vaccine Mediates Superior Antitumor Responses1", The Journal of Immunology, 170:4242-4253 (2003).

Pravin T.P. Kaumaya, et al., "Design and Immunological Properties of Topographic Immunogenic Determinants of a Protein Antigen (LDH-C4) as Vaccines", The Journal of Biological Chemistry, vol. 267, No. 9, Mar. 25, 1992, pp. 6338-6346.

Susan Kobs-Conrad, et al., Engineered Topographic Determinants with alpha-beta, beta-alpha-beta, beta-alpha-beta-alpha and Topologies Show High Affinity Binding to Native Protein Antigen (Lactate Dehydrogenase-C4), The Journal of Biological Chemistry, vol. 268, No. 34, Dec. 5, 1993, pp. 25285-25295.

Paolo Calabresi, et al., "Ionotropic Glutamate Receptors: Still a Target for Neuroprotection in Brain Ischemia? Insights from In Vitro Studies", Neurobiology of Disease, 12 (2003): pp. 82-88.

International Search Report from PCT/US07/09753 dated Dec. 26, 2007.

International Search Report and Written Opinion from PCT/US06/02403 dated Dec. 4, 2007.

Lautermann, J., "Glautathione-Dependent Antioxidant Systems in the Mammalian Inner Ear: Effects of Aging, Ototoxic Drugs and Noise", Hear Res., Dec. 1997, 114 (1-2) p. 75, Abstract.

U.S. Appl. No. 11/780,853, filed Jul. 20, 2007.

U.S. Appl. No. 11/831,230, filed Jul. 31, 2007.

Konishi, T., et al. (1973), "Effect of Potassium Deficiency on Cochlear Potentials and Cation Contents of the Endolymph", Acta Otolaryng 76:410-8.

Feng, B., et al., (2004), "Structure-Activity Analysis of a Novel NR2C/NR2D-Preferring NMDA Receptor Antagonist: 1-(phenanthrene-2-carbonyl) piperazine-2,3-dicarboxylic acid", Br. J. Pharmacol. 141:508-516.

Geneste P., et al. (1979) "Détermination conformationnelle de dérivés de la phenycyclidine en vue d'une corrélation structure-activité", Eur. J. Med Chem. 14:301-308.

Hansen, R.E., et al., (1988) "Determination of the Regime of Rapid Reacting Systems in Stopped- and Steady-flow Investigations by the Velocity Probe Method", J. Phys. Chem. 92:2189-2196.

Lu Y, et al. (2004) "Micro and Nano-Fabrication of Biodegradable Polymers for Drug Delivery", Adv. Drug Deliv. Rev. 56:1621-1633.

Morris A.W., et al. (1989), "Cochlear Dialysis for Meniere's Disease", An Update. Am J. Otol. 10:148-9.

Muly S.M., et al. (2004) "Noise Trauma Alters D-[3H]aspartate Release and AMPA Binding in Chinchilla Conchlear Nucleus", J. Neurosci. Res. 75:585-596.

Orive G., et al., (2005) "Micro and Nano Drug Delivery Systems in Cancer Therapy", Cancer Therapy 3:131-138.

Prakobvaitayakit M., et al. (2003) "Optimization of polylactic-co-glycolic Acid Nanoparticles Containing Itraconizole Using 23 Factorial Design", AAPS PharmaSciTech 4(4):Article 71 (http://www.aapspharmascitech.org).

Takizawa S., et al. (1995), "A Selective N-type Calcium Channel Antagonist Reduces Extracellular Glutamate Release and Infarct volume in Focal Cerebral Ischemia", J. Cerebral Blood Flow Metab. 15:611-8.

Mizukoshi, et al., "Drug Delivery to the Cochlea Using Poly Lactic/glycolic Acid Nanoparticles", Abstracts of the Twenty-Ninth Annual Midwinter Research Meeting, Feb. 5-9, 2006, ARO Abstracts, vol. 29, 2006, 5 pages.

Sun, et al., "Neurotrophin-3 Gene Transfection of Cochlear Cells with hydroxyapatite Nanoparticle Vector", Abstracts of the Twenty-Ninth Annual Midwinter Research Meeting, Feb. 5-9, 2006, ARO Abstracts, vol. 29, 2006, 5 pages.

Pedrini, et al., "Evaluation of Thrombogenicity of Fluoropassivated Polyester Patches Following Carotid Endarterectomy", Nov. 2001 Ann. Vasc. Surg. 15(6):679-83.

Kim, et al., "An Experimental Study on Thrombogenicity of Various Metallic Microcoils with or without Thrombogenic Coatings" Jul. 1998, Invest. Radiol. 33(7):407-410.

Hong, et al., "Material-Specific Thrombin Generation Following Contact Between Metal Surfaces and Whole Blood", Apr. 2005, Biomaterials 26(12):1397-403.

Salt A.N., et al., (1998) "Longitudinal Endolymph Movements Induced by Perilymphatic Injections", Hearing Research 123:137-147.

Feijen R.A., et al., (Mar. 1, 2002) "Change of Guinea Pig Inner Ear Pressure by Square Wave Middle Ear Cavity Pressure Variation", Acta Otolaryngologica, 122:No. 2:138-45.

Sennaroglu L., et al., (Sep. 2001) "Relationship of Vestibular Aqueduct and Inner Ear Pressure in Meniere's Disease and the Normal Population", Laryngoscope 111:1625-1630.

Salt An, et al., (2003), "Contamination of Perilymph Sampled from the Basal Cochlear Turn with Cerebrospinal Fluid", Hearing Research 182:24-33.

U.S. Appl. No. 61/022,224, filed Jan. 18, 2008.

Rodrigues CM, et al., (2003), "Tauroursodeoxycholic Acid Reduces Apoptosis and Protects Against Neurological Injury After Acute Hemorrhagic Stroke in Rats", Proc Natl Acad Sci USA 100:6087-6092.

Unsolicited email, purporting to be from Elson Silva, received May 4, 2008 by Applicants' representative.

U.S. Appl. No. 11/008,869, filed Dec. 9, 2004.
U.S. Appl. No. 11/016,604, filed Dec. 16, 2004.
U.S. Appl. No. 11/089,171, filed Mar. 24, 2005.
U.S. Appl. No. 11/122,648, filed May 5, 2005.
U.S. Appl. No. 11/139,296, filed May 26, 2005.
U.S. Appl. No. 11/178,054, filed Jul. 8, 2005.
U.S. Appl. No. 11/226,777, filed Sep. 13, 2005.
U.S. Appl. No. 11/261,432, filed Oct. 28, 2005.
U.S. Appl. No. 11/262,055, filed Oct. 28, 2005.
U.S. Appl. No. 11/386,198, filed Mar. 21, 2006.

International Search Report and Written Opinion for PCT/US07/13686 dated Jul. 23, 2008.

International Search Report and Written Opinion for PCT/US07/19385 dated Jul. 28, 2008.

International Search Report and Written Opinion for PCT/US07/16414 dated Aug. 12, 2008.

Hoizey, et al., "Distribution of Gacyclidine Enantiomers after Experimental Spinal Cord Injury in Rats", J. of Pharm. Sci., vol. 90, No. 1, pp. 70-78.

International Search Report and Written Opinion for PCT/US07/17109 dated Aug. 22, 2008.

International Preliminary Report on Patentability for PCT/US2007/009753 dated Nov. 4, 2008.

International Preliminary Report on Patentability for PCT/US2007/013686 dated Dec. 10, 2008.

Office action mailed Dec. 22, 2008 in U.S. Appl. No. 11/831,230.

Gould, et al., International Journal of Pharmaceutics, 33 (1986), pp. 201-217.

Hirbec, et al., "Gacyclidine: A New Neuroprotective Agent Acting at the N-Methyl-D-Aspartate Receptor", CNS Drug Reviews, vol. 7, No. 2, pp. 172-198, 2001.

Supplementary European Search Report for EP07755859 dated Jun. 9, 2010.

* cited by examiner

US 7,803,148 B2

FLOW-INDUCED DELIVERY FROM A DRUG MASS

CROSS-REFERENCE TO RELATED APPLICATIONS

This application claims the benefit of U.S. Provisional Application Ser. No. 60/804,394, filed Jun. 9, 2006 and titled "Drug Delivery by Flow Dissolution," hereby incorporated by reference herein.

BACKGROUND

Use of drugs in combination with devices capable of tissue-specific delivery poses special problems for drug formulation. In some cases, the formulation should be stable over an extended period of time, especially if that formulation is intended for use in an implanted drug delivery device.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

At least some embodiments of the invention address problems posed by tissue-specific drug delivery devices. In at least some such embodiments, a solid form of a drug is stored in the device and delivered to a desired region using an appropriate vehicle. Embodiments of the invention also include preparing a solution (or suspension) of a therapeutically effective concentration of a drug which is sparingly soluble in water, with the solution (or suspension) being formed by removal of drug from a mass of solid drug using an appropriate vehicle.

BRIEF DESCRIPTION OF THE FIGURES

The following detailed description is better understood when read in conjunction with the accompanying drawings, which are included by way of example, and not by way of limitation. Some of the drawings include shading. Shading is provided only for the purpose of enhancing readability, and the presence or absence of shading in a particular drawing is not otherwise intended to have significance.

DETAILED DESCRIPTION

Figure 1:
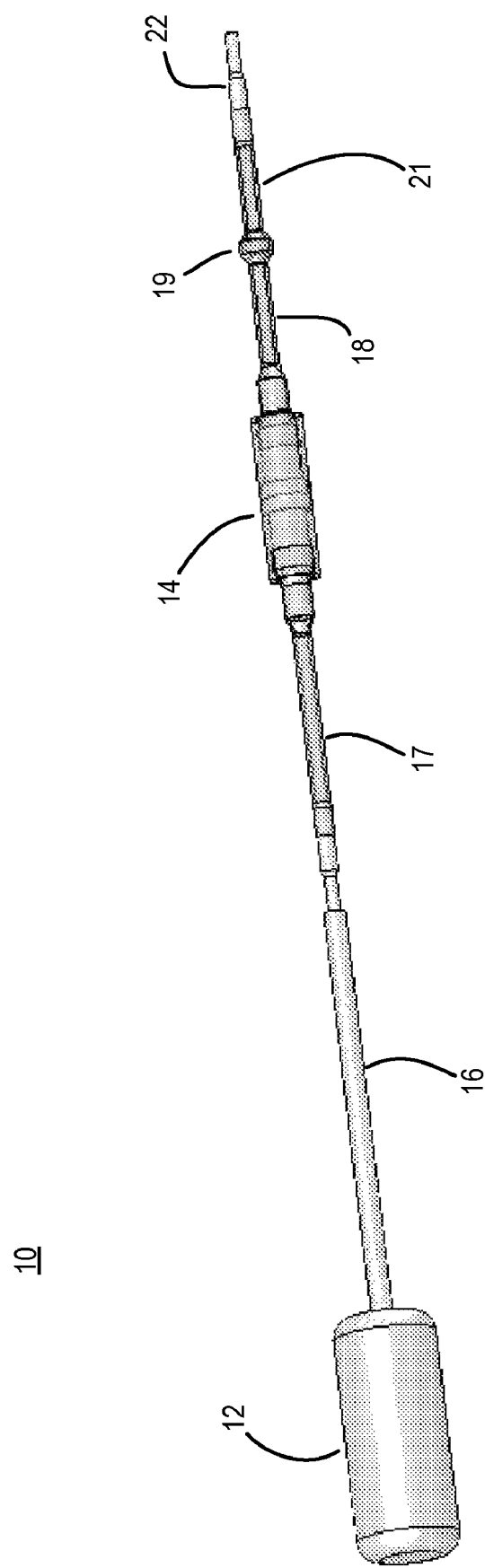
FIG. 1 shows a drug delivery device according to one embodiment.

At least some embodiments include methods for delivering a therapeutically effective concentration of a drug for which either the acidic or basic form of the drug is water insoluble or sparingly water-soluble. As used herein, a drug form is "sparingly water-soluble" if only an insignificant amount of that drug form can be dissolved by water alone. For a drug with acid-base functional groups, a less water-soluble form is likely to be more stable than a form of the drug which is water-soluble. This is a consequence of such a form being less prone to solution-dependent decomposition processes, especially if the drug is stored as a solid (e.g., in a crystalline state). Moreover, a crystalline or amorphous solid drug will often occupy a smaller volume than is required for another form of the drug. This can facilitate construction of small delivery devices and/or reservoirs for storing a drug. When a drug is stored in solid form, properties of a vehicle can be used to control the rate at which drug is removed (whether by dissolution, elution, erosion or some other mechanism or combination of mechanisms) from one or more masses of solid drug, thereby offering a flexibility for modulating a concentration of drug that is delivered to a tissue or other target region.

As used herein (including the claims), a "vehicle" is a fluid medium used to remove solid drug from one or more masses of solid drug and/or to deliver the removed drug to a target tissue or to some other desired location. A vehicle can be a bodily fluid, an artificial fluid or a combination of bodily and artificial fluids, and may also contain other materials in addition to a drug being removed and/or delivered. A vehicle may contain such other materials in solution (e.g., NaCl in saline, a solution of an acid or base in water, etc.) and/or suspension (e.g., nanoparticles). Further examples of vehicles are included below.

Drug that is removed from a solid drug mass by a vehicle and retained in that vehicle is sometimes referred to herein as being entrained within (or by) the vehicle. As used herein (including the claims), "entrained" drug includes drug that is eroded from a mass and dissolved in the vehicle, drug that is eroded from a mass and suspended in the vehicle, and drug that is eroded from a mass and adsorbed/absorbed to nanoparticles or other components of the vehicle. A drug that is removed from a solid drug mass and remains within the vehicle in another chemical form (e.g., a salt that results when a basic solid drug mass is placed into contact with an acidic vehicle) is also included within the scope of the phrase "entrained drug."

According to at least some embodiments in which the basic form of a solid drug is less soluble than an acidic solid form, solid pellets of the basic form are eluted with an acid at a concentration that is substantially the same as the desired drug concentration. In at least some embodiments in which the acidic form of a drug is less soluble than the basic form, solid pellets of the acidic form are eluted with a base at a concentration that is substantially the same as the desired drug concentration. According to at least some additional embodiments, an aqueous solution comprising one or more components having an amphipathic molecule which can solubilize a water-insoluble drug can be used to erode a solid drug pellet to effect delivery of a therapeutically effective amount of the drug.

At least some embodiments also include a drug reservoir which can contain one or more masses of one or more solid drugs. The solid drug can be eluted from the reservoir with an appropriate solution or other vehicle capable of effecting solid drug dissolution or otherwise capable of removing small amounts of drug from the one or more solid drug masses at a desired rate.

An advantage of using solid drug in an implanted device is, in at least some embodiments, the ability to store drug in the device using a smaller volume than might be required if a premixed (or other liquid) form of the drug were used. In some cases, this smaller volume enables implantation of a device containing enough drug to provide (when combined with an appropriate vehicle source) substantially continuous long term therapy. This long term therapy can be over a period of days, weeks, or months. In some cases, long term therapy may extend over several years. One example of a basic crystalline or solid amorphous drug suitable for use in methods according to some embodiments is gacyclidine. It is estimated that 18 mg of gacyclidine will deliver 100 µM drug over 4 years at a flow rate of 20 microliters per hour. The hydrochloride salt of gacyclidine, its acidic form, is highly water soluble. However, the acidic form of gacyclidine is also unstable at body temperature. By contrast, the basic form of gacyclidine is sparingly soluble in water and is much more stable than its acidic form in the presence of water. Dissolution of the basic form of gacyclidine in water requires the presence of an acid (e.g., hydrochloric acid or lactic acid) to convert the basic form to the water-soluble acidic form. The concentration of gacyclidine in solution will therefore depend on the amount of acid available to convert the basic form to the acid form. This ability of an appropriate vehicle to change the amount of drug dissolved and delivered offers substantial flexibility in changing the concentration of delivered drug, without requiring the changing of a device holding the solid drug, and without loading a different concentration of a therapeutic solution into a liquid reservoir.

One example of an acidic crystalline drug that is suitable for use in methods according to some other embodiments is carbamathione. See U.S. Patent Application Publication No. 2005/0130904. Carbamathione contains four acid-base functionalities: two carboxylic acids, one thiol group, and one amino group. In its monobasic-triacidic form, carbamathione will readily form crystals that are sparingly soluble in water. Dissolution of this form of the drug in water requires one equivalent of base, such as sodium bicarbonate or sodium hydroxide, to convert this form to the dibasic-diacidic form, which is water soluble.

Methods of the invention are not limited to delivery of gacyclidine or carbamathione. At least some embodiments include methods applicable to delivery of any drug which is water (or other vehicle) soluble in one of an acid or base form and sparingly soluble in the other of the acid or base form. A solid comprised of the less water soluble drug form is eluted or eroded with a compatible vehicle (e.g., Ringer's solution, Ringer's lactate, saline, physiological saline, artificial perilymph) comprising, as appropriate, either an acid or a base. If the less water-soluble drug form is a basic form, then the vehicle can contain a pharmaceutically acceptable acid, such as hydrochloric acid, monobasic sodium phosphate (e.g., monosodium phosphate), lactic acid, phosphoric acid, citric acid, a sodium salt of citric acid, or lactic acid. If the less water-soluble drug form is an acidic form, then the vehicle can contain a pharmaceutically acceptable base, such as sodium hydroxide, sodium bicarbonate, or choline hydroxide.

Methods according to at least some embodiments of the invention can employ solid drug pellets. Those pellets can be crystalline masses or solid amorphous masses. One example of manufacturing drug pellets is included herein as Example 1. A solid drug could also include a combination of crystalline and amorphous masses. The drug can be melt molded into any desired shape or can be pressed into pellets using pressure. Crystalline drug (if available) may be more desirable than amorphous solid drug forms in some cases, as crystalline substances typically are more stable. Crystal lattice energy may also help stabilize the drug. However, the invention is not limited to crystalline drug forms or the use thereof.

The invention is not limited to drugs (or to methods or devices employing drugs) with acid-base functionalities. Embodiments also include dissolution (or removal from a mass by other mechanism) of any drug which is sparingly soluble in water by eluting the drug with a pharmaceutically acceptable vehicle (e.g., saline, Ringer's lactate, artificial perilymph, Ringer's solution) comprising one or more components having an amphipathic molecule, such as monopalmitoyl glycerol or polysorbate 80 (e.g., TWEEN 80®). Other suitable amphipathic molecule components include (but are not limited to) an acyl glycerol, a poly-oxyethylene ester of 12-hydroxysteric acid (e.g., SOLUTOL® HS15), beta-cyclodextrin (e.g., CAPTISOL®), a bile acid such as taurocholic acid, tauroursodeoxycholic acid, cholic acid or ursodeoxycholic acid, a naturally occurring anionic surfactant such as galactocerebroside sulfate, a naturally occurring neutral surfactant such as lactosylceramide or a naturally occurring zwitterionic surfactant such as sphingomyelin, phosphatidyl choline or palmitoyl carnitine. Dissolution (or other removal) can also be accomplished by use of physiological fluid vehicles, such as cochlear perilymph, cerebrospinal fluid, or interstitial fluid. Physiological fluid vehicles contain amphipathic molecules, such as proteins and lipids, which are capable of effecting dissolution of a water-insoluble drug. Dissolution can also be carried out without the use of an amphipathic molecule where an acceptable concentration of drug is obtained.

One example of a drug that does not have acid-base functionalities is triamcinolone acetonide. Triamcinolone acetonide is commercially available as a crystalline solid with very low water solubility. If solid pellets of triamcinolone acetonide are exposed to a continuous stream of a vehicle, such as Ringer's solution, the expected concentration of extracted triamcinolone acetonide in solution should be 40 µM or less. A higher concentration of triamcinolone acetonide can be solubilized by including an amphipathic molecule in the vehicle. Such a pharmaceutically acceptable amphipathic molecule would be polysorbate 80. The concentration of triamcinolone acetonide solubilized can be increased above its water solubility, 40 µM, by adding the required amount of amphipathic molecule to the vehicle that will support the desired drug concentration. The invention is not limited to methods implemented through use of triamcinolone acetonide, Ringer's solution or polysorbate 80. Any sparingly soluble drug, pharmaceutically acceptable vehicle and pharmaceutically acceptable amphipathic molecule can be used.

Nanoparticles can maintain a drug in a mobile phase capable of passing through an antibacterial filter. Some embodiments would use, in place of or in combination with an amphipathic drug carrier, a suspension of particles (e.g., nanoparticles) that would have affinity for a drug (e.g., that would adsorb/absorb a drug) and act as carriers. Still other embodiments include use of pure drug nanoparticles. Yet other embodiments include combinations of both pure drug nanoparticles and drug adsorbed/adsorbed to carrier nanoparticles. Particles according to at least some embodiments would be small enough to pass through an antibacterial filter of 0.22 microns or less. Removal of a drug from a mass thereof using a vehicle having suspended carrier nanoparticles would be advantageous to both drug stability and delivery. Removal of solid drug from a mass of drug nanoparticles would have similar benefits.

As indicated above, in at least some embodiments a vehicle includes a suspension of small carrier particles (100 nm to 0.1 mm in size) or carrier nanoparticles (10 nm to 100 nm in size) having an affinity for the drug(s) to be delivered. Examples of materials from which the carrier particles or nanoparticles could be formed include (but are not limited to) polylactic acid, polyglycolic acid, a co-polymer of lactic acid and glycolic acid, polypropylene, polyethylene and polystyrene. Additional examples of materials from which carrier particles or nanoparticles can be formed include magnetic metals and magnetic metals having a coating to attract a drug (or drugs) of interest. These small carrier particles or nanoparticles will adsorb/absorb or otherwise attract drug that is eroded from a mass of solid drug (which may be stored in a reservoir such as is described herein) by a vehicle in which the carrier particles (or nanoparticles) are suspended.

In some embodiments, a vehicle will be to used to erode pure drug nanoparticles from a solid mass composed of such pure drug nanoparticles. Such a solid mass of nanoparticles could be formed by compression and/or by use of a binder.

In some cases, a small amount of acid or amphipathic excipient (e.g., SOLUTOL® HS15, TWEEN 80® or CAPTISOL®) can be employed to facilitate drug removal from a mass of solid drug (or from a mass of solid drug nanoparticles) and transfer to a mobile nanoparticle suspension.

In some embodiments, polymeric material used to fabricate carrier nanoparticles is biodegradable (so as to help promote ultimate delivery of drug), commercially available and approved for human use. Polymers of L- and D,L-lactic acid and copolymers of lactic acid and glycolic acid [poly (lactide-co-glycolide)] (available from Lakeshore Biomaterials in Birmingham, Ala.) are examples of polymeric materials that have the potential to meet the desired properties of the polymer for carrier nanoparticles. Nanoparticles small enough to pass through a 0.22 µm antibacterial filter have been fabricated from a 50:50 mix of poly(lactide-co-glycolide) by the solvent replacement method.

Several methods have been employed to fabricate nanoparticles of suitable size. These methods include vaporization methods (e.g., free jet expansion, laser vaporization, spark erosion, electro explosion and chemical vapor deposition), physical methods involving mechanical attrition (e.g., pearl-milling), interfacial deposition following solvent displacement and supercritical $CO_2$. Additional methods for preparing nanoparticles include solvent displacement of a solubilizing solvent and a solvent in which the nanoparticle is not soluble, vibrational atomization and drying in the atomized state, sonication of two liquid streams, use of micropumps (such as ink jet-like systems delivering nano and micro-sized droplets of drug) and continuous flow mixers.

When preparing nanoparticles by the solvent displacement method, a stirring rate of 500 rpm or greater is normally employed. Slower solvent exchange rates during mixing produce larger particles. Fluctuating pressure gradients are fundamental to producing efficient mixing in fully developed turbulence. Sonication is one method that can provide adequate turbulent mixing. Continuous flow mixers (two or more solvent streams) with and without sonication may provide the necessary turbulence to ensure small particle size if the scale is small enough. The solvent displacement method has the advantage of being relatively simple to implement on a laboratory or industrial scale and has produced nanoparticles able to pass through a 0.22 µm filter. The size of nanoparticles produced by the solvent displacement method is sensitive to the concentration of polymer in the organic solvent, to the rate of mixing and to the surfactant employed in the process.

Pure drug nanoparticles can be prepared by neutralization of a dissolved acid or basic drug or dilution of the dissolved drug (in insoluble form) with a miscible solvent in which the drug is not soluble. With rapid mixing and the introduction of the precipitating solvent at the correct speed for that particular drug, nanoparticles are produced. Alternatively, drug nanoparticles can be derived from atomized microparticles that were dried while suspended in a drying gas and collected. Solid nanoparticle masses suspended in a solvent (for example, composed of pure basic gacyclidine) can be isolated by accelerated sedimentation rates with a centrifuge (e.g., a Hermle Z229 centrifuge operating at 15,000 rpm with an average g force of 30,000 g (25,000 g to 35,000 g)) either with a binding agent to facilitate the pellet formation or by mixing later with the binding agent and/or by compression of a dried pellet. There is a correlation between particle size and sedimentation rate according to Stoke's Law [$v=D^2(\rho_p-\rho_1)g/18\eta$]. At one gravity, the time required for sedimentation of a 100 nm particle will be about 200 days, while a 10 nm particle will take approximately six years to settle out. The exact time required for sedimentation will depend on particle density ($\rho_p$), liquid density ($\rho_1$), liquid viscosity ($\eta$) and particle diameter (D). Once isolated the dried or wet pellet of drug particles can be compressed into a solid mass or mixed with a pharmaceutically acceptable binder and compressed into a mass.

In at least some embodiments, a device employed for removal of drug from a solid drug mass with (and entrainment by) a vehicle can include any chamber capable of holding a less water-soluble form of the drug and permitting a vehicle comprising a dissolving or other removal agent (e.g., acid, base, an amphipathic molecule, a suspension of nanoparticles) to flow past the solid drug. The size of the chamber, rate of vehicle flow and concentration of acid, base, amphipathic molecule or nanoparticles used are determined by the intended application of the drug delivery device and dissolution characteristics (or erosion or other physical characteristics) of the drug substance and/or drug mass, as well as by any required vehicle reservoir and/or pumping system. Determination of the parameters for such a device is within the ability of one skilled in the art, once such a person is provided with the information included herein.

Fluid flow to effect drug dissolution (or removal by other mechanism) can be accomplished by any pump with fluid flow parameters that match the desired application. Such pumps include, but are not limited to, syringe pumps (e.g., the MiniMed 508 pump described below in Example 2), a MEMS pump, an osmotic pump, a peristaltic pump, a piston pump, piezo-electric pump and the like. Selection of an appropriate pump is similarly within the ability of one skilled in the art, once such a person is provided with the information included herein. In some embodiments, a pump can be fully implanted within a human (or other animal) body. In other embodiments, a pump may be external to the body and delivering vehicle through a subcutaneous port or other connection to a reservoir holding solid drug.

In at least some embodiments, solid drug can be removed from a mass thereof using a liquid that is delivered from an implanted or external source containing a fluid such as saline, Ringer's solution, Ringer's lactate, or artificial perilymph in order to dissolve or otherwise load the drug into the liquid. The drug-laden liquid solution is then delivered to the target tissue. Examples of target tissues include, but are not limited to, a cochlea, lymph nodes, tumors, a brain, a spine, etc.

In at least some embodiments, a fully implantable drug delivery device includes a fluid delivery device, such as an osmotic pump, in fluid communication with a drug-containing chamber and a three-dimensional antibacterial filter. One embodiment is shown in FIG. 1. In the embodiment of FIG. 1, device 10 includes an osmotic pump 12 coupled to a sleeved drug reservoir 14 via a catheter 16 and 17. A three-dimensional (3-D) antibacterial filter 19 is coupled to drug reservoir 14 via a catheter 18. Another catheter 21 and connector 22 connects 3-D filter 19 via an additional catheter (not shown) to a terminal component (also not shown) positioned for delivery of a drug-laden solution into the target tissue. The terminal component may be, e.g., a needle, a cochlear implant electrode, a cochlear catheter, or even an open end of a catheter. Drawing FIG. 1 from U.S. patent application Ser. No. 11/414,543 (filed May 1, 2006 and titled "Apparatus and Method for Delivery of Therapeutic and other Types of Agents") illustrates an embodiment where the terminal component is a bone needle. Prior to implantation, the osmotic pump is filled with a solution that will dissolve the solid drug.

Figure 2:
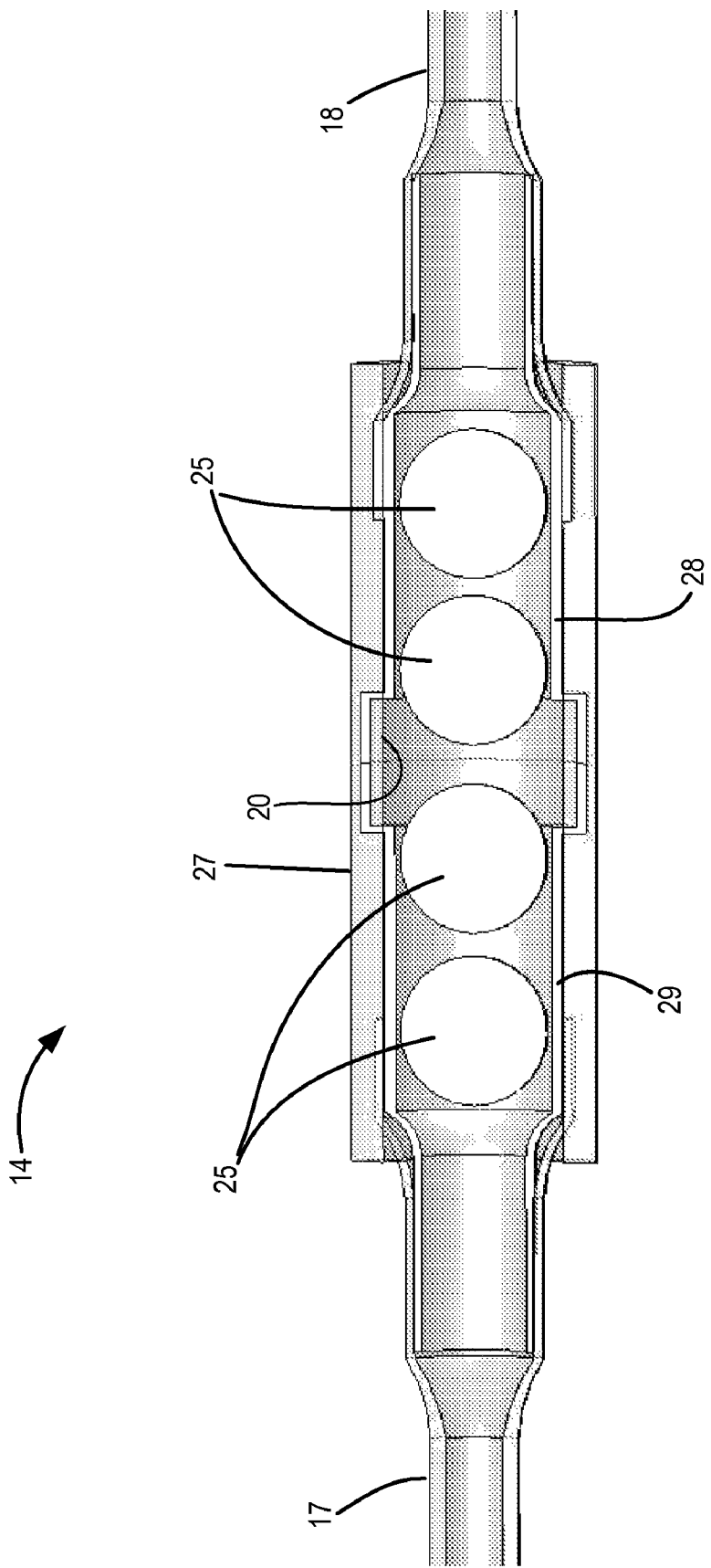
FIG. 2 is a cross-sectional view of a sleeved drug chamber from FIG. 1.

A solid drug reservoir is designed to provide a cavity for fluid to flow around and erode one or more masses of solid drug (e.g., solid drug pellets). FIG. 2 is a cross-sectional view of sleeved drug reservoir 14 of FIG. 1, which is but one example of a drug reservoir according to at least some embodiments. Drug reservoir 14 includes two hollow metal tubes 28 and 29 (made from a drug compatible material) forming a chamber 20 into which multiple solid drug pellets 25 are loaded. A sleeve 27 (made from silicone or other appropriate material) is rolled over tubes 28 and 29 to form a liquid tight seal. Tapered ends of tubes 28 and 29 fit into ends of catheters 18 and 17, respectively. Drug reservoir 14 of FIG. 2 is shaped to contain the drug pellets within chamber 20 and prevent solid pieces from moving out of chamber 20. Drug reservoir 14 may also be pulled apart and reattached to thereby allow loading of one or more solid drug pellets.

Figure 3A:
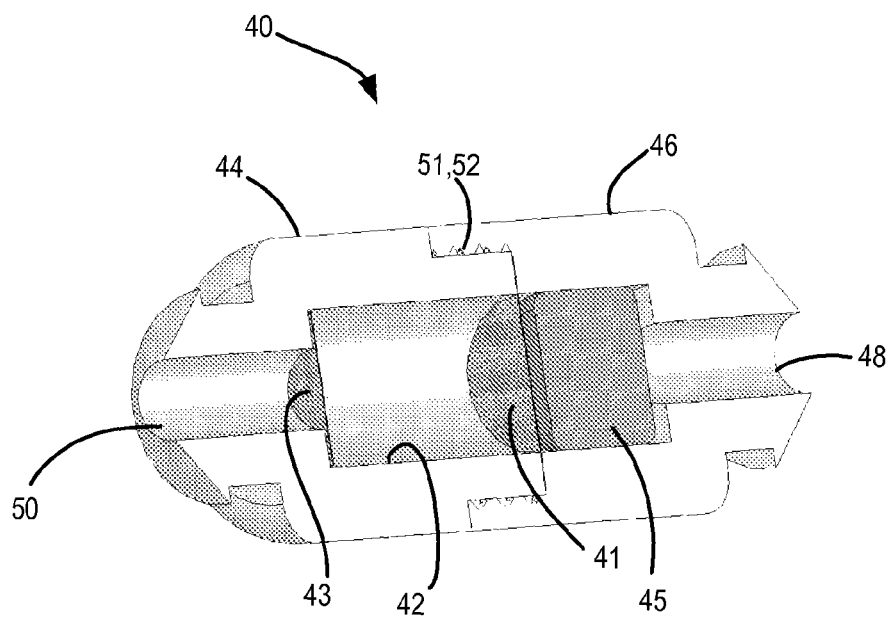
FIGS. 3A through 3C are cross-sectional views of drug chambers including screens.
Figure 3B:
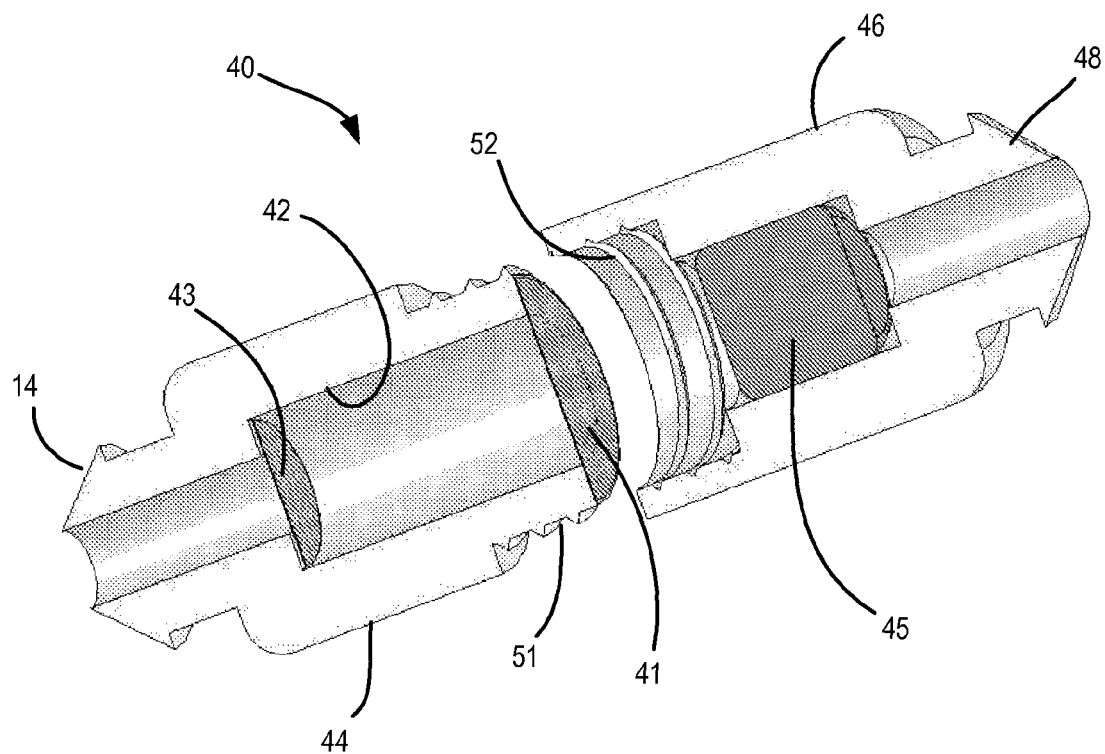

In some embodiments, circular screens are placed inside a drug chamber to further prevent migration of drug pellets. In some cases, at least one of the screens may be removable to allow for replenishment of drug. FIGS. 3A and 3B are cross-sectional views of a drug reservoir 40 according to another embodiment, and that includes such screens. As seen in FIGS. 3A and 3B, drug reservoir 40 includes housings 44 and 46 that mate together (with threads 51 and 52) to form a fluid-tight connection. Solid drug can be placed inside chamber 42 within housing 44, with housing 44 including a stationary meshed screen 43 on the side of tubing connection inlet 50 and a removable meshed screen 41 at the edge of housing 44. As seen in FIG. 3A, screen 41 is directly before 3-D antibacterial filter 45, which rests within housing 46. Screens 41 and 43 are porous and may be woven wire cloth made of titanium, stainless steel, or biocompatible, drug compatible polymers such as fluoropolymers. In other embodiments, the screens may be made of porous metal, such as titanium or stainless steel. Meshed screens 41 and 43 prevent drug pellets from going into the housing 46, antibacterial filter 45 or tubing (not shown) that may be connected to inlet connection 50 or outlet connection 48. In FIG. 3A drug reservoir 40 is shown with housing halves 44 and 46 threaded together. FIG. 3B shows housings 44 and 46 separated, but with removable screen 41, stationary screen 43 and antibacterial filter 45 in place. As seen in FIG. 3B, removable screen 41 covers the outer circular surface of the end of housing 44. Stationary screen 43 only covers the inner circular surface of space 42. Screens can be of any shape to fit the shape of the drug chamber. Screens are not required, however, and may be omitted in certain embodiments.

Figure 3C:
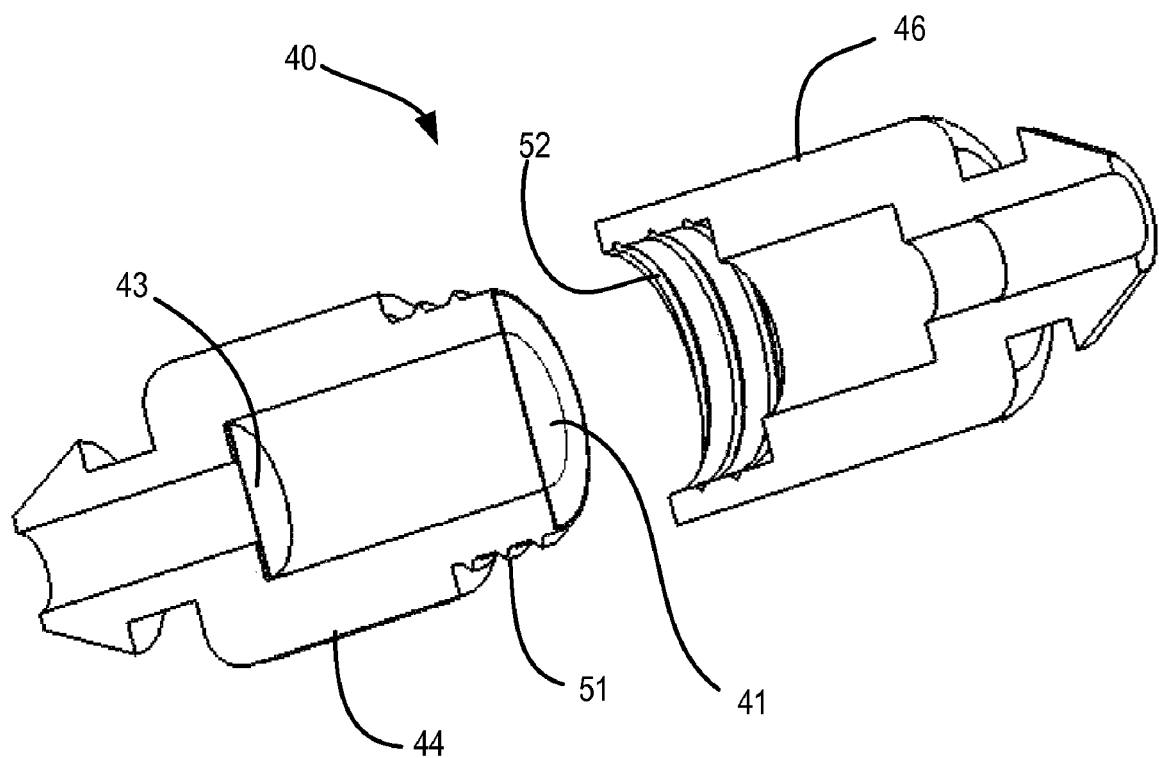

An antibacterial filter is similarly not required. For example, FIG. 3C is a cross-sectional view of drug reservoir 40 without antibacterial filter 45. At least some embodiments may also include features which permit air bubbles to bleed off during filling of the system. This can help to prevent vapor lock in cases where a fluid delivery system (e.g., an osmotic pump or an external pump) does not generate sufficient pressure to overcome surface tension holding liquid within capillary-like structures of a wet porous filter (such as 3-D filter 45 of FIGS. 3A and 3B). In some embodiments, a set screw or plug may be incorporated into the side of a drug chamber housing on the upstream (i.e., higher pressure) side of the filter. The set screw or plug may be removed during priming and reattached for use once all air bubbles have been bled from the system. In still other embodiments, a vent valve may include an upstream semi-permeable membrane allowing for venting of gases. In yet other embodiments, the set screw or plug may be non-removable, but may include a portion which is gas-permeable but not liquid-permeable so as to allow degassing.

Figure 3D:
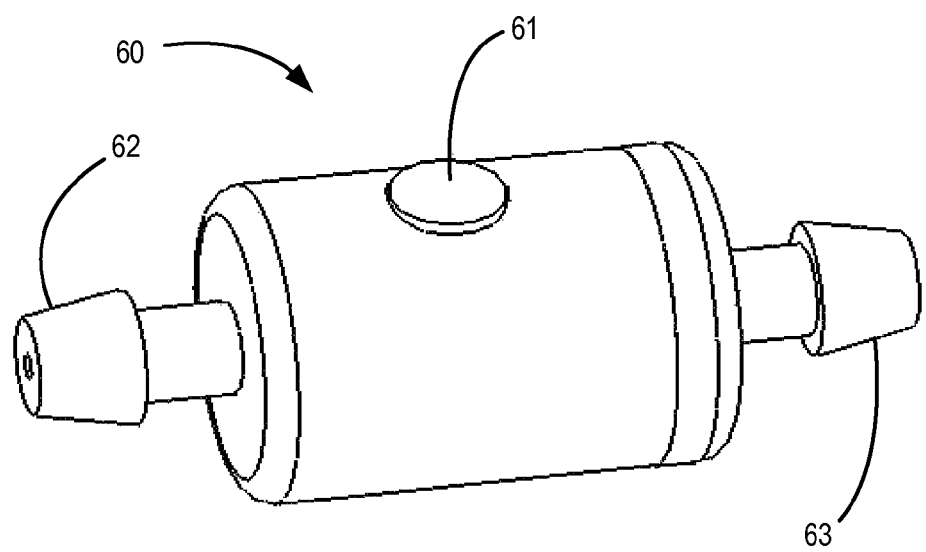
FIGS. 3D and 3E are perspective and cross-sectional views, respectively, of a drug chamber that includes an air vent.
Figure 3E:
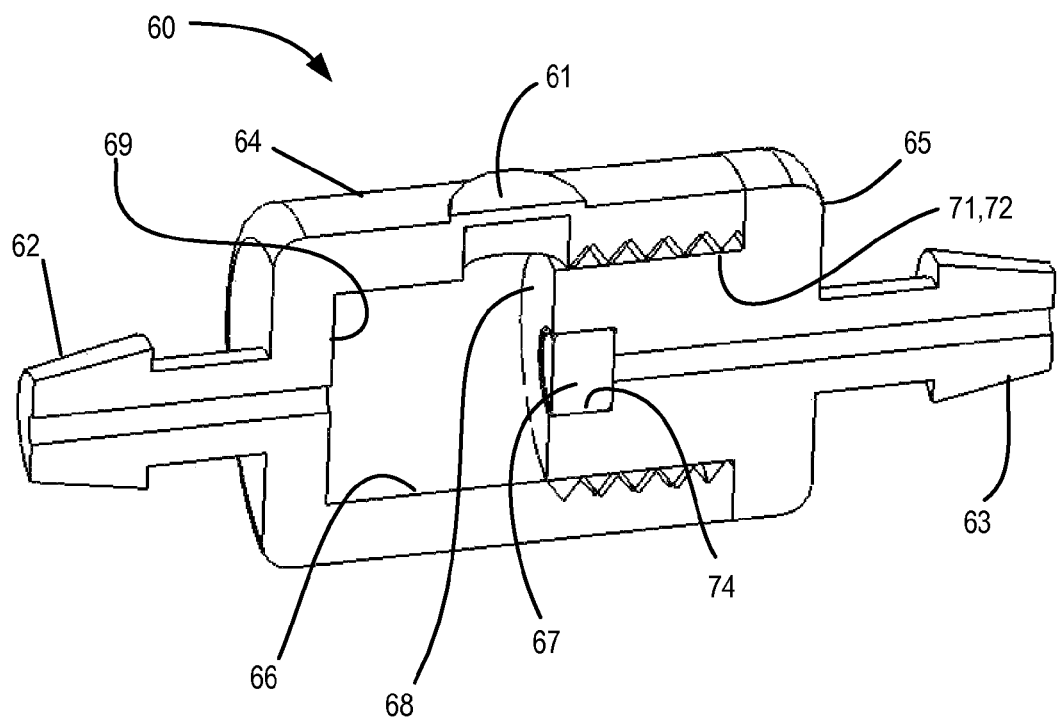

FIG. 3D shows a drug reservoir 60 according to at least one embodiment, and which includes vent valve 61 having a semi-permeable membrane allowing for venting of gases. Tubing connector barb 62 is on the upstream side of reservoir 60, and tubing connector 63 is on the downstream side. FIG. 3E is a cross sectional view of drug reservoir 60. Drug reservoir 60 includes housings 64 and 65 which join to form a fluid-tight connection with threads 71, 72. A cavity 66 holds one or more solid drug pellets or other masses. Although not shown, screens similar to screens 43 and 41 in FIGS. 3A and 3B can be placed (in either a stationary or removable configuration) over face 69 on the upstream side of space 66 and over face 68 on the downstream side of space 66. In the embodiment of FIG. 3D, a 3-D antibacterial filter 67 fits within a space 74 formed in housing 65.

Housings 44 and 46 of drug reservoir 40, housings 64 and 65 of drug reservoir 60, and housings of drug reservoirs in other embodiments can be made of a drug-compatible, corrosion-resistant material such as titanium, stainless steel, a biocompatible coated metal, a chemically inert polymer such as PTFE, FEP, PFA and other fluoropolymers or a fluoropolymer-coated metal. During low flow rates at body temperature, drug may tend to adsorb to the walls of the chamber, causing lower than expected concentrations of drug to be delivered to the patient. Fluoropolymers are the best known materials for resisting adsorption.

Figure 3F:
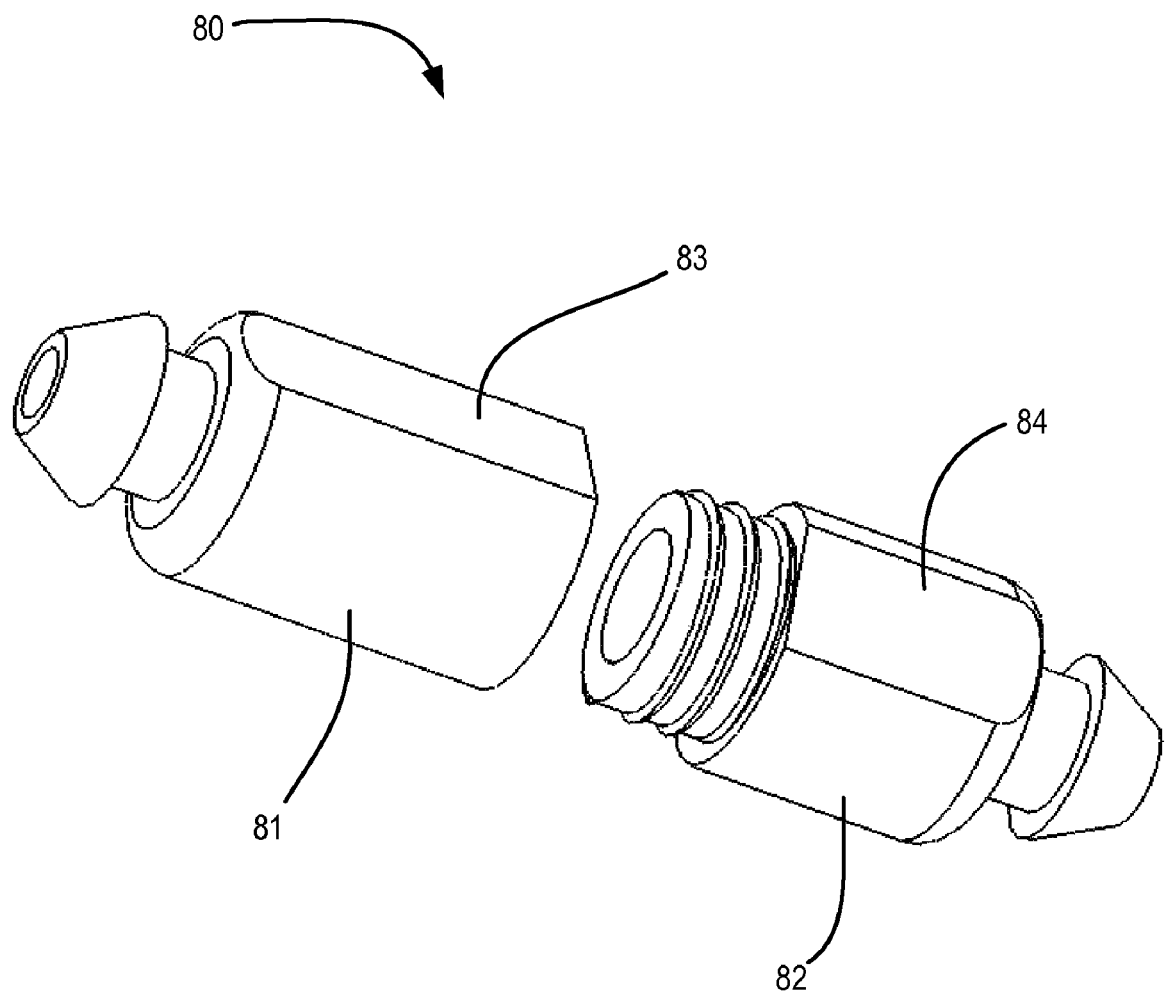
FIG. 3F is a perspective view of a drug chamber that includes flats.

As indicated above, drug reservoirs in various embodiments may be opened and closed to allow for replenishment of solid drug. The reservoir components may be threaded (as shown in FIGS. 3A-3C and 3E) or may consist of a locking tab and groove. In still other embodiments an external clamp may be used. In yet other embodiments, reservoir housings may be joined by a snap-fit. As also indicated above, reservoir 14 (FIG. 2) includes two metal tubes 28 and 29 held together by a surrounding sleeve 27. Surrounding sleeve 27 may be made of a flexible polymer such as silicone rubber. In some embodiments, a biocompatible gasket can be placed between mating portions of a drug reservoir (e.g., between tubes 28 and 29 of FIG. 2, between housings 44 and 46 of FIGS. 3A-3C, between housings 64 and 65 of FIG. 3E) to prevent leaks. In still other embodiments, external portions of a drug reservoir housing may include flats or other regions to facilitate easier tightening. FIG. 3F shows an embodiment of a drug reservoir 80 having mating housings 81 and 82. A flat 83 is formed on one side of housing 81. A second flat (not shown) can be formed on an opposite side of housing 81. Similarly, housing 82 includes a flat 84 formed on one side, and can also include an additional flat (also not shown) on an opposite side.

In at least some embodiments, catheter tubing on the upstream side of a drug reservoir (e.g., tubing for catheter 16 on the pump side of device 10 in FIG. 1) is a vehicle- and biocompatible, flexible polymer such as silicone, polyurethane, or fluoropolymer including PTFE, FEP, and PFA and the catheter tubing on the downstream side of the drug reservoir is a biocompatible, drug compatible, flexible polymer such as PTFE, FEP and other fluoropolymers.

Figure 4:
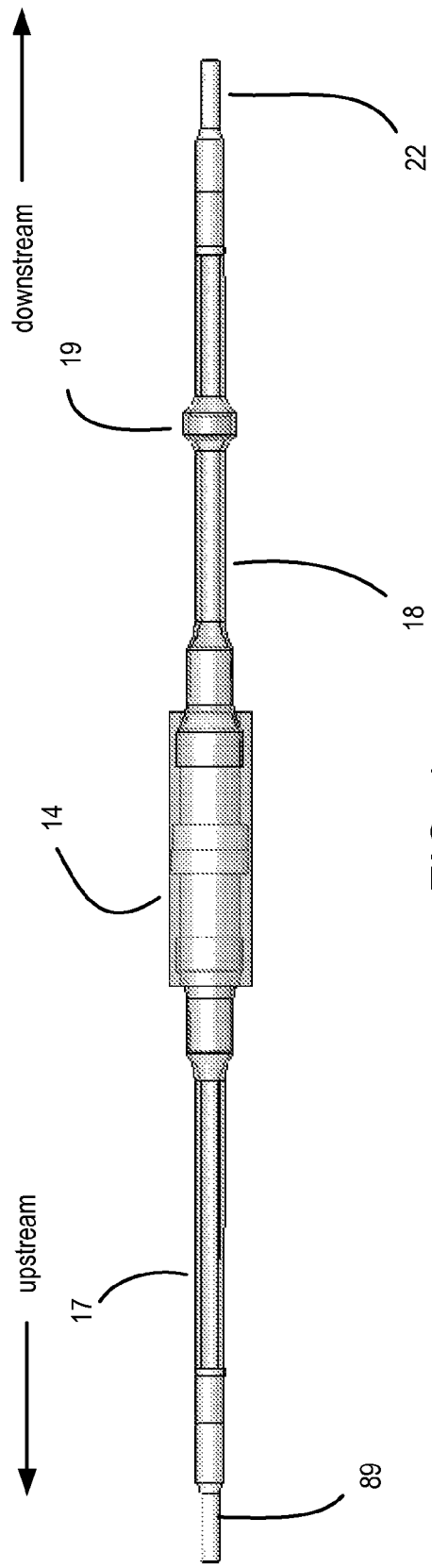
FIG. 4 shows a sleeved drug chamber joined to catheters and to a 3-D antibacterial filter.
Figure 5:
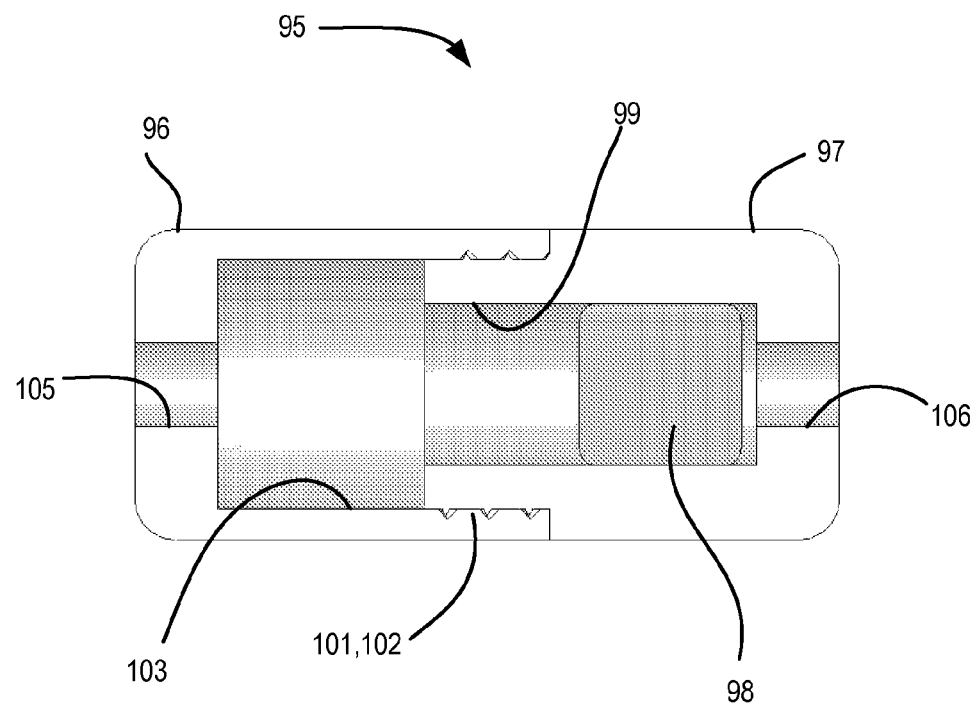
FIG. 5 is a cross sectional view of a solid drug and 3-D antibacterial filter housing.

In some embodiments, the solid drug reservoir and a 3-D antibacterial filter are in fluid communication via catheter connection. This is seen generally in FIG. 1, and in more detail in FIG. 4 (where upstream and downstream directions are indicated). Also shown in FIG. 4 are metal tubing connectors 22 and 89 that can be used to connect to upstream or downstream components. In another embodiment, a single housing may contain solid drug as well as a three-dimensional antibacterial filter. One example of such a configuration can be seen in drawing FIG. 2 from commonly-owned U.S. patent application Ser. No. 11/414,543 (titled "Apparatus and Method for Delivery of Therapeutic and Other Types of Agents" and filed May 1, 2006), the housing for which holds a separate container (a cage in that case) for drug. Such a housing may also be opened and closed to allow for replenishment of solid drug. FIG. 5 is a cross-sectional view of a drug reservoir 95 according to another embodiment. Drug reservoir 95 includes housings 96 and 97 joined by mating threads 101, 102. A cavity 103 inside housing 96 holds solid drug (not shown). Screens similar to screens 41 and 43 of FIGS. 3A and 3B may also be included. A 3-D antibacterial filter 98 is located in a space 99. Instead of the barbed fittings shown in FIGS. 3A-3F, drug reservoir 95 includes an upstream inlet hole 105 and a downstream inlet hole 106.

Figure 6:
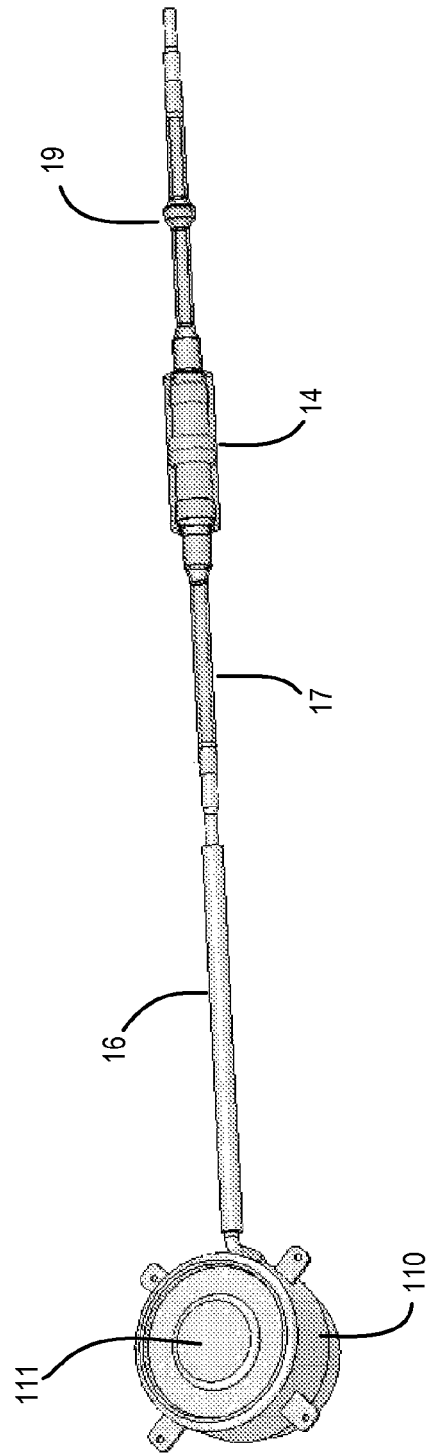
FIG. 6 shows a subcutaneously-implantable port attached with a catheter to a sleeved drug chamber.
Figure 7:
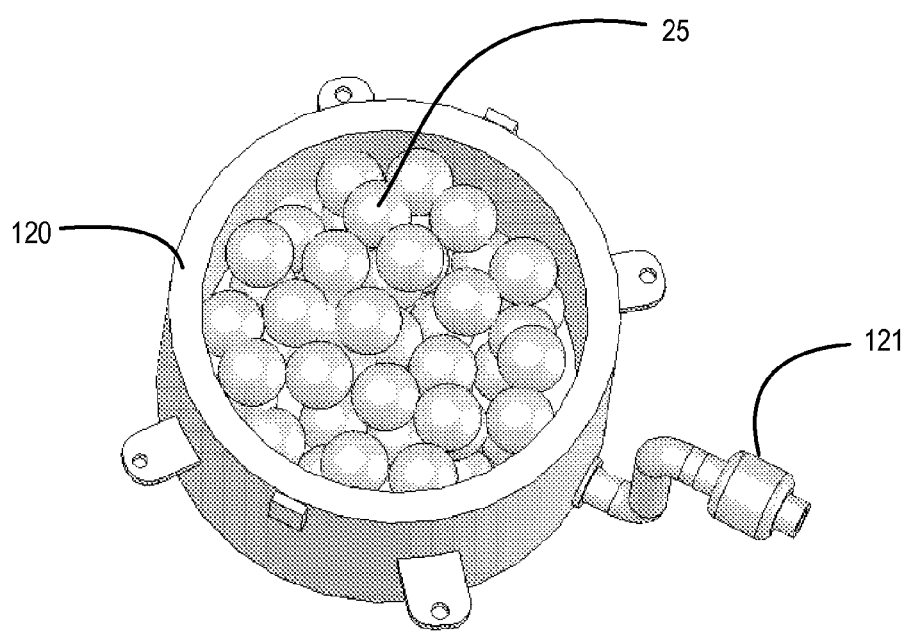
FIG. 7 shows an open subcutaneously-implantable port containing pellets of solid drug.

In some embodiments the solid drug reservoir is a subcutaneously-implantable port (or is in fluid communication with such a port). One such embodiment is shown in FIG. 6, where osmotic pump 12 of device 10 (FIG. 1) has been replaced with a subcutaneous port 110. In other embodiments, a subcutaneously-implantable port reservoir contains solid drug pellets which are eroded by a vehicle that is introduced into the port via a needle that pierces a septum of the port (with the needle in fluid communication with an external pump or some other source of vehicle). FIG. 7 shows a subcutaneously-implantable port 120 with its cover (and septum) removed, and containing solid drug pellets 25. As also shown in FIG. 7, a 3-D antibacterial filter 121 may be attached to an outlet of port 120.

A 3-D antibacterial filter could alternatively be located elsewhere between the drug-holding cavity of port 120 and the distal end of a catheter delivering drug from port 120. The shape of the solid drug can be molded into any appropriate shape.

In at least some embodiments, a housing for a drug and filter is made from titanium and is small enough to be implanted into a human body. The inner diameter is sized so that a 3-D antibacterial filter can be bonded to the inside of the housing. Examples of possible filter sizes (in various embodiments) include but are not limited to 0.2 micron pore size 3-D filters with a physical outer diameter of 0.03 to 0.25". In still other embodiments the physical outer diameter is between 0.1" and 0.3".

Figure 8:
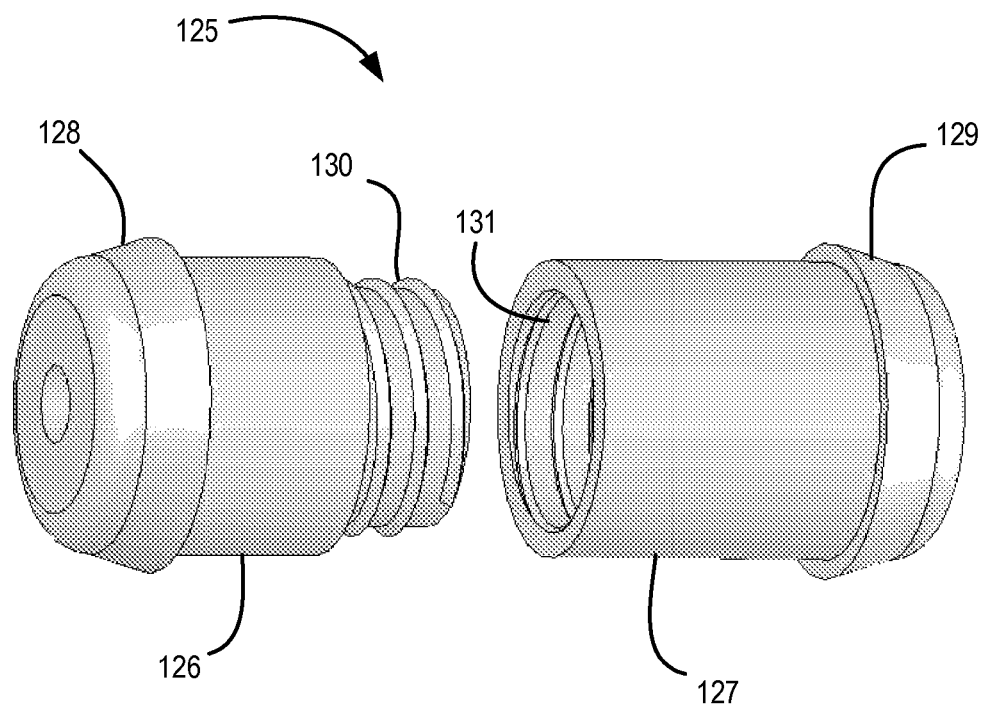
FIGS. 8 and 9 show a two piece solid drug and 3-D antibacterial filter housing according to another embodiment.
Figure 9:
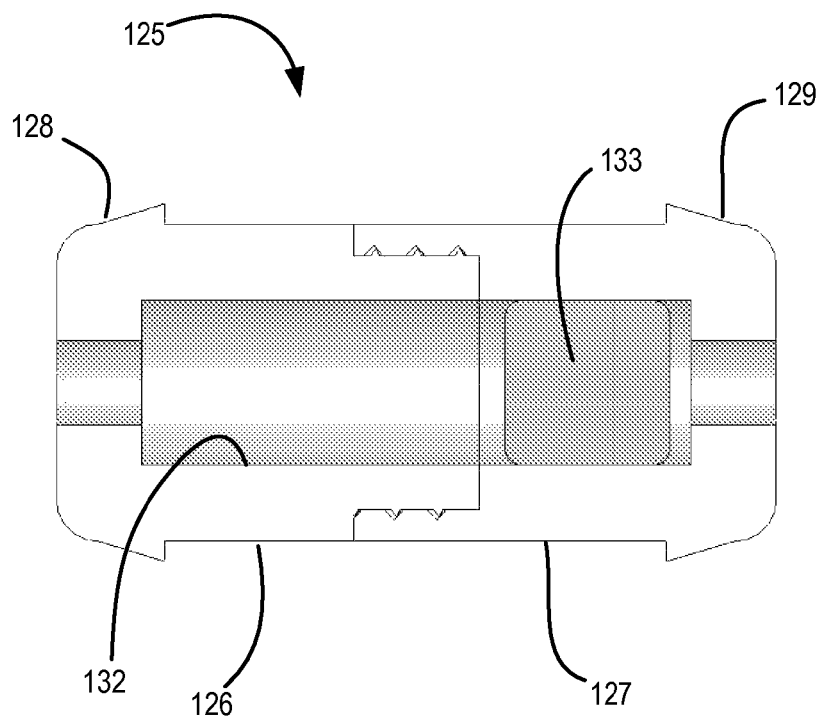

FIG. 8 is a perspective view of two separated housings 126 and 127 a drug reservoir 125 according to at least one embodiment. FIG. 9 is a cross-sectional view of drug reservoir 125, with housings 126 and 127 joined (via threads 130 and 131). The entire outer ends of housings 126 and 127 have barbs 128 and 129 (respectively) formed thereon. Also seen in FIG. 9 are a space 132 for holding solid drug and an optional 3-D antibacterial filter 133.

Figure 10:
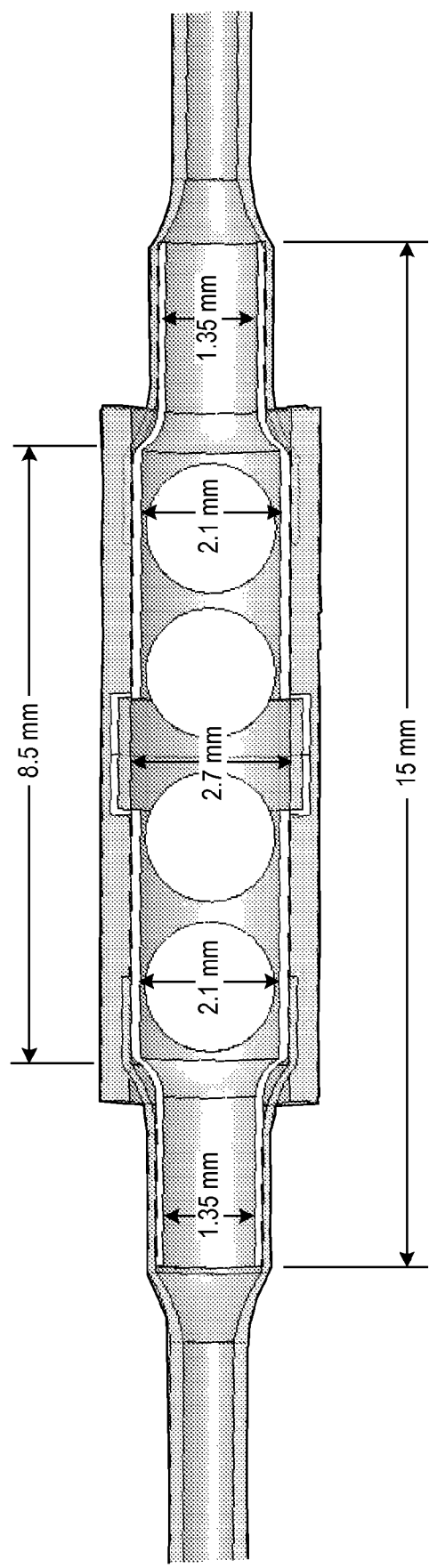
FIG. 10 is a cross-sectional view of the sleeved drug chamber from FIG. 2, with example dimensions included.

FIG. 10 is a cross-sectional view of sleeved drug reservoir 14 from FIGS. 1 and 2, and with example dimensions included. In the example of FIGS. 1, 2 and 10, the interior chamber 20 volume is approximately 43 mm$^3$ (43 µL), with approximately 32 mm$^3$ available to hold solid drug.

Figure 11:
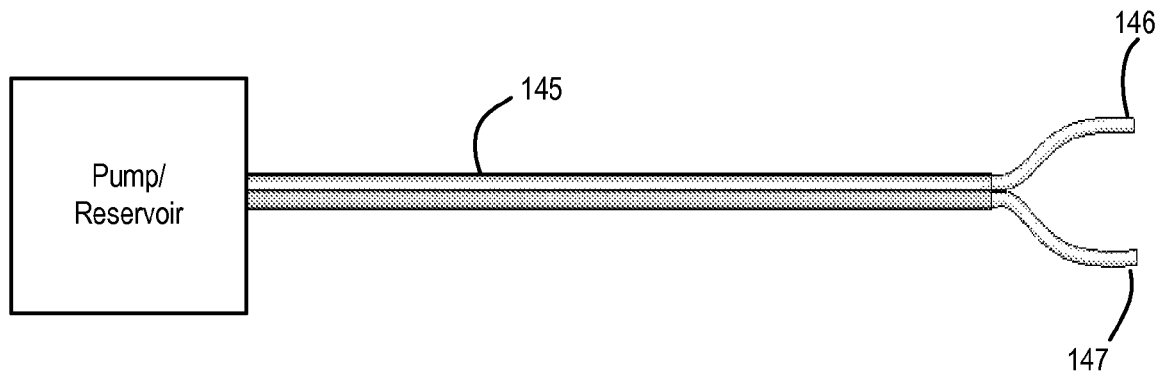
FIG. 11 shows an embodiment in which a dual lumen tube extends from a pump and/or reservoir containing solid drug.
Figure 12:
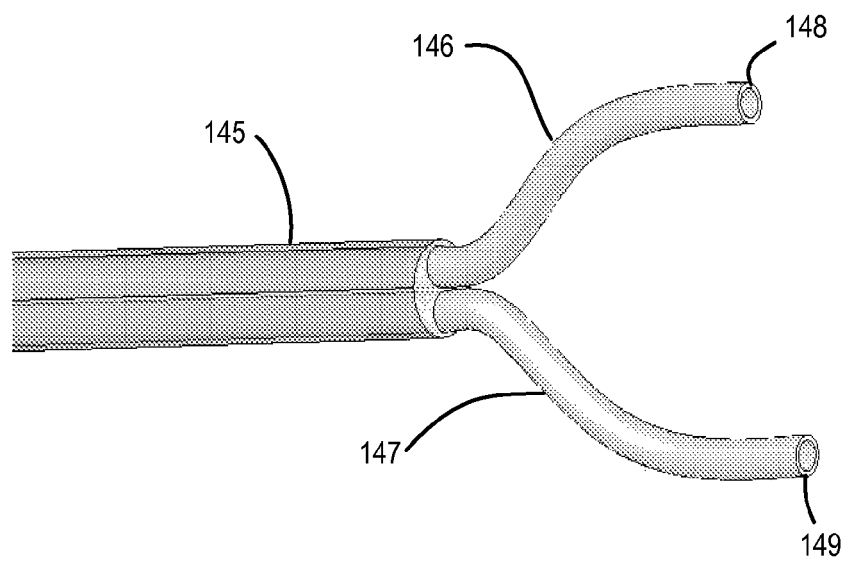
FIG. 12 is an enlarged view of the distal ends of the dual lumen tube shown in FIG. 11.

FIG. 11 shows an additional embodiment in which a dual lumen tube 145 extends from a pump and/or reservoir containing solid drug. Dual-lumen tube 145 separates into two separate lines. Tube 146 is attached to one lumen and receives inflowing physiological fluid from a patient. Tube 147 is attached to another lumen and delivers therapeutic fluid to the patient. Physiological fluid received in line 146 flows past solid drug pellets in the reservoir and slowly removes (e.g., by dissolution) drug from those pellets. The resulting solution of drug and physiological fluid is then delivered to a target tissue through tube 147. FIG. 12 is an enlarged view of the distal ends 148 and 149 of tubes 146 and 147, and further illustrates the two lumens for recirculating fluid flow. In other embodiments, two completely separate tubes (i.e., two tubes that do not emerge from a dual lumen tube) may be used. Such an embodiment could be useful in cases where physiological fluid is withdrawn from a region that is more distant from the region in which therapeutic fluid is to be delivered.

Figure 13:
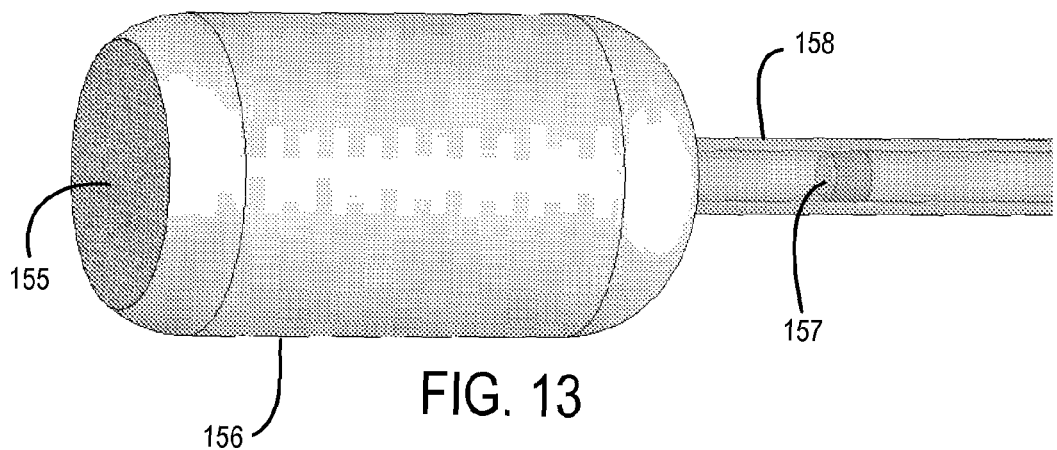
FIG. 13 is a perspective view showing an embodiment in which a semi-permeable membrane allows interstitial fluid to pass into a chamber containing a solid drug.
Figure 14:
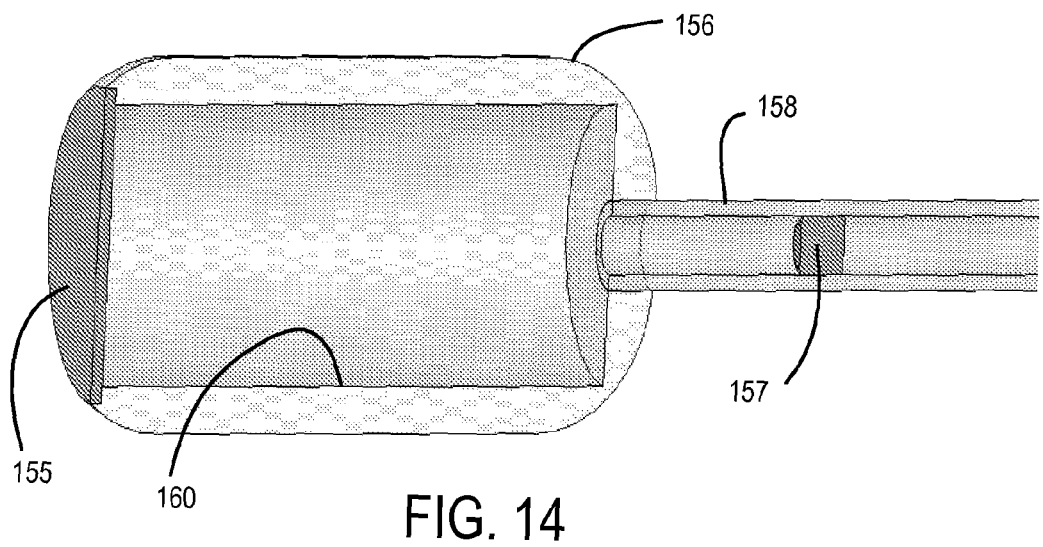
FIG. 14 is a fully cross-sectional view of the embodiment of FIG. 13.
Figure 15:
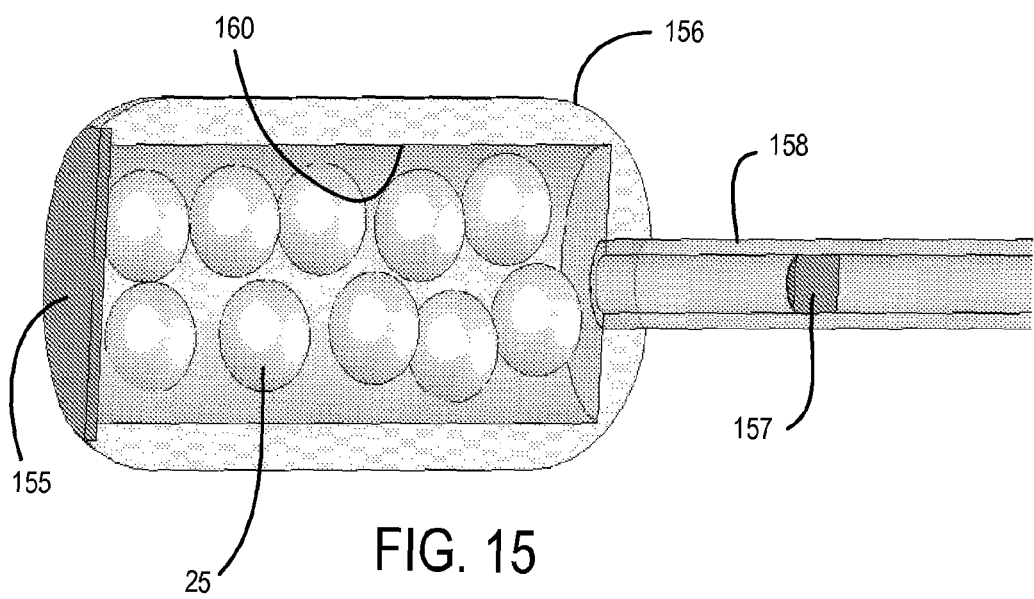
FIG. 15 shows the embodiment of FIGS. 13 and 14 containing solid drug pellets.

FIG. 13 is a perspective view showing an embodiment of a system which does not require a pump to generate flow. A semi-permeable membrane 155 allows an interstitial fluid vehicle to pass into a chamber of a reservoir 156 containing solid drug. As drug within the chamber dissolves (or is otherwise removed from the solid drug mass and entrained in the interstitial fluid vehicle), the concentration difference across the membrane causes fluid to flow from low concentration to higher concentration. Osmotic pressure forces fluid past membrane 155, into the drug chamber, through the outlet, and past an optional 3-D antibacterial filter 157 in a catheter 158 (shown as a clear catheter for purposes of illustration) to the target delivery site. Semi-permeable membrane 155 has a pore size cutoff sufficient to let interstitial fluid through but not let the entrained solid drug diffuse out. Antibacterial filter 157 has pores sufficient to retain bacteria but to let dissolved (or otherwise entrained) drug pass through. An electric field may also be applied to membrane 155 resulting in diffusion by electro-osmosis. FIG. 14 is a fully cross-sectional view of the embodiment of FIG. 13, and shows in more detail a cavity 160 for holding a solid drug. FIG. 15 shows the embodiment of FIGS. 13 and 14 containing solid drug pellets 25 in cavity 160. Appropriate check valves (not shown) can be included within cavity 160 or elsewhere in the fluid path so as to prevent backflow.

Figure 16:
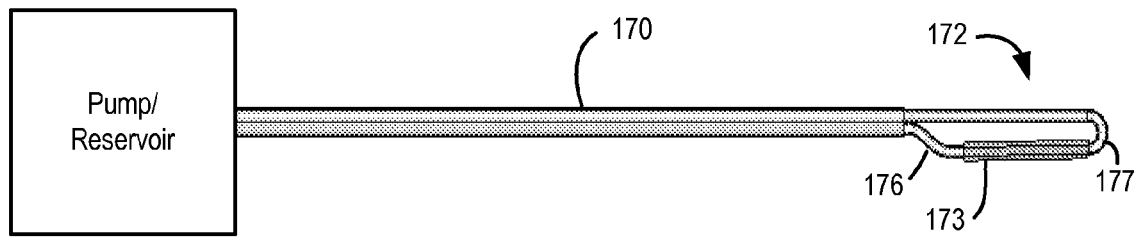
FIG. 16 shows an embodiment where fluid is circulated unidirectionally through a loop containing a semi-permeable hollow fiber.
Figure 17:
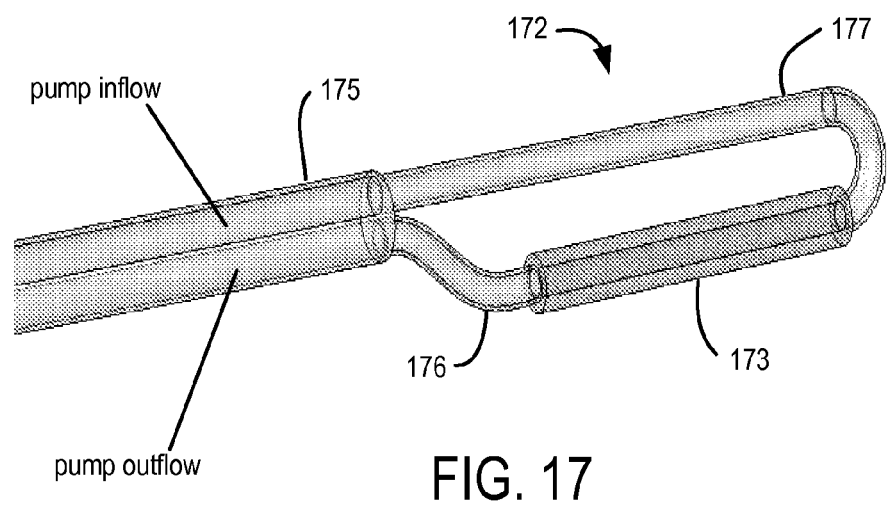
FIG. 17 is an enlarged view of the distal end of the embodiment of FIG. 16, and shows additional details of the hollow fiber loop.
Figure 18:
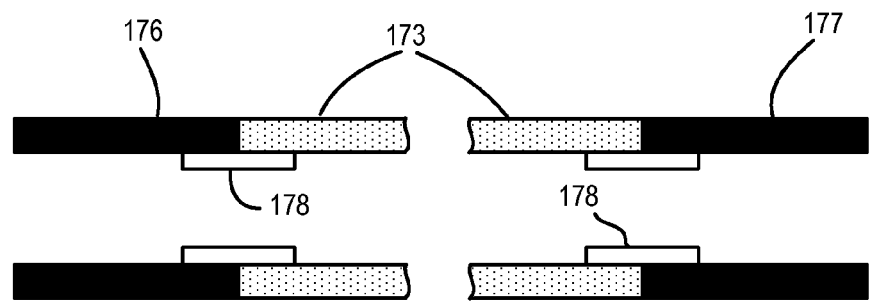
FIG. 18 is a cross-sectional view of the connection between the hollow fiber and non-permeable tubing of FIG. 17.

FIG. 16 shows an embodiment of a system 170 where fluid is circulated unidirectionally from a pump/reservoir (via one lumen of dual-lumen tubing 175) through a loop 172 containing a semi-permeable hollow fiber 173 and returned through a second lumen of tubing 175. Hollow fiber loop 173 is a terminal component which can be positioned at a target delivery area. The pump circulates vehicle past solid drug located in the reservoir, and the resulting drug-loaded vehicle diffuses through the walls of hollow fiber 173 into the target tissue. FIG. 17 is an enlarged view of hollow fiber loop 172 shown in FIG. 16, with the various components made partially transparent for purposes of explanation. Loop 172 containing hollow fiber 173 is attached to respective inflow and outflow lumens in dual-lumen tube 175 with non-permeable tubing sections 176 and 177. FIG. 18 is a cross-sectional view of the connection between hollow fiber 173 and non-permeable tubing sections 176 and 177. Connectors 178 may be made of titanium, stainless steel, or other biocompatible, drug compatible metals or polymers.

Still other embodiments include pH and/or round window noise sensors (e.g., an ultra micro microphone) with attached battery and power electronics (power supply, recharging circuitry, etc.) and communication electronics to receive and send information. In these embodiments, the electronics could be bundled with the reservoir section of the device and the sensors could be combined with a wire following the surface of the catheter or contained within one of the lumens of a multi-lumen tubing and exiting within a cochlea or other target tissue.

At least some embodiments include electrophoresis-stimulated delivery of charged drug ions or other particles of drug. For charged drugs, applying an electric field on a fluid containing the drug (or containing nanoparticles that have adsorbed/absorbed drug) can induce the migration of the drug faster than normal diffusion. In the case of gacyclidine, a negative charge on a device exit (e.g., at the end of a catheter) or just outside of a device exit can be used to accelerate the drug delivery to the cochlea or any other target tissue without the need for a pump. A same or similar charge of opposite polarity (e.g., a positive charge in the case of gacyclidine) could similarly be applied to a drug containing compartment (e.g., a chamber in which solid drug is held), thereby enabling drug delivery out of the device without the need for a pump. The electrophoresis environment would induce an electro-osmotic flow to the natural low resistance outlet within the cochlea or target tissue. The rate of migration of drug to the catheter tip (or the concentration of drug) could be modulated by field strength of the electric charge and other parameters modulated by an appropriate electronics package, battery, recharging assembly, on/off switch, communication circuitry and other electronics. If a drug having an opposite charge is used, then the electronic circuitry would reverse the charges on the electrodes. Electrophoresis-stimulated drug delivery embodiments would be very low power devices in order to promote patient safety, and because small amounts of drug are being delivered. A charged device in a cochlea may provide additional benefits to tinnitus patients who report benefit from electrical stimulation. Indeed, in some embodiments a catheter includes an electrode that is only used for delivery of electrical stimulation (pulsed or otherwise) to a cochlea. In still other embodiments, a catheter includes an electrode that is alternatively (or additionally) used to sense noise, electrical potential or some other physical characteristic in a cochlea or in some other target tissue. Methods and electronics for such stimulation and/or sensing are known in the art (although not in combination with the drug delivery devices described herein). Because inclusion of appropriate stimulation and/or sensing electronics into the herein-described drug delivery systems would be within the routine skill of a person of ordinary skill in the art once such a person is provided with the information contained herein, additional details of such stimulation and/or sensing electronics is not included.

Figure 19:
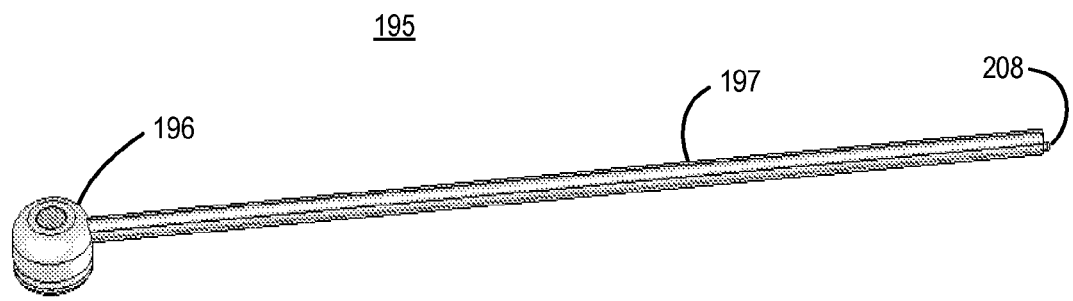
FIGS. 19 through 22 show an embodiment implementing electrophoresis-stimulated delivery of drug.
Figure 20:
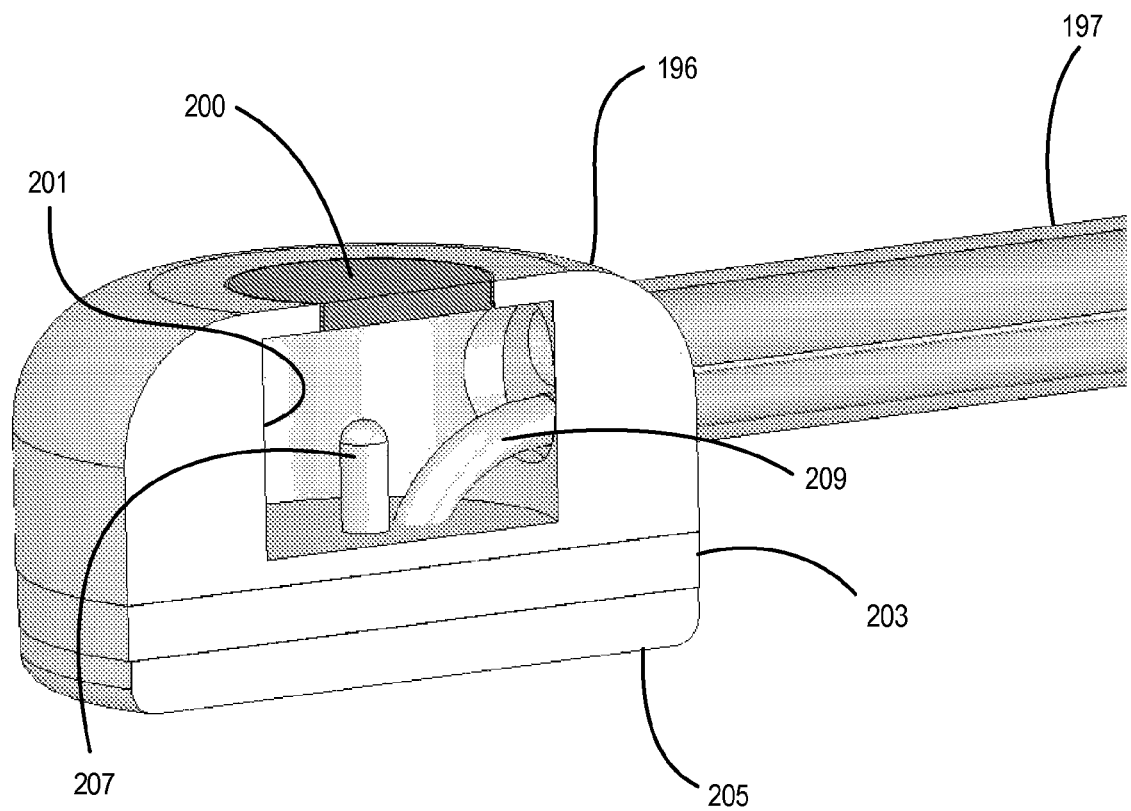
Figure 21:
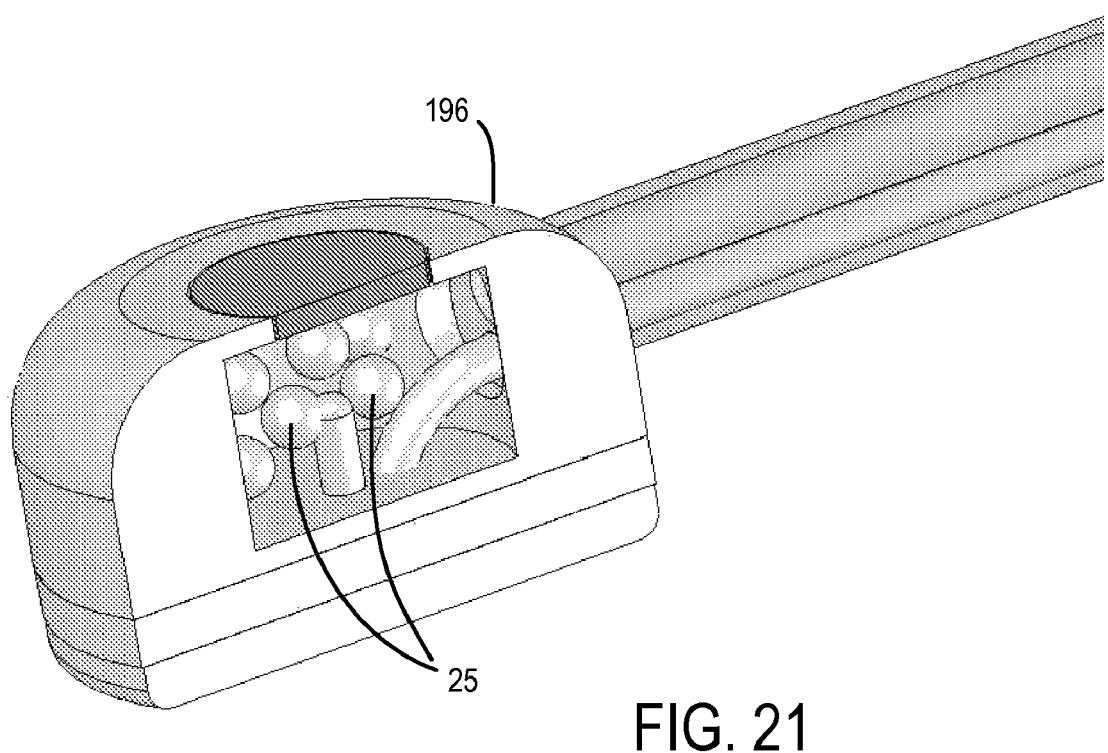
Figure 22:
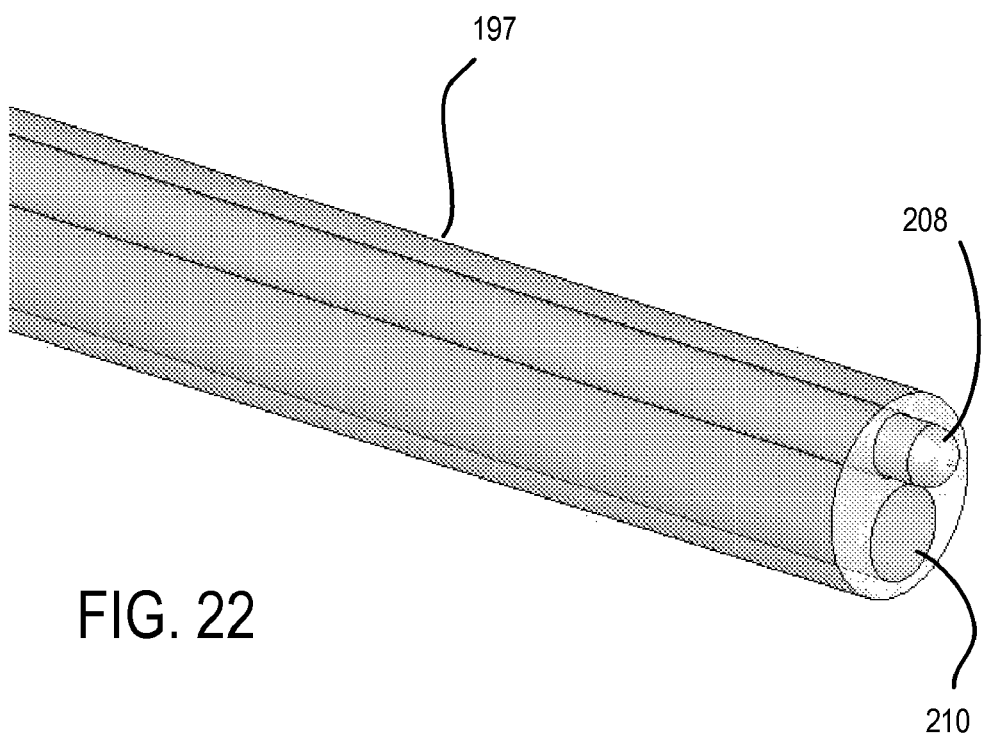

FIG. 19 shows an electrophoresis-stimulated drug delivery system 195 according to at least some embodiments. Tube 197 contains a fluid delivery lumen and an electrode wire, and extends from drug reservoir 196. FIG. 20 is a cross-sectional view of drug reservoir 196 and a portion of tube 197. Reservoir 196 includes a semi-permeable membrane 200 and an internal cavity 201 for holding solid drug pellets. An electronics package 203 and battery 205 are attached to the underside of reservoir 196. Electronics package 203 induces a charge of one polarity in electrode tip 207 and a charge of opposite polarity in a tip 208 (see FIGS. 19 and 22) of electrode wire 209. The portion of wire 209 within cavity 201 may be coated with a dielectric or otherwise insulated to prevent premature charge exchange with tip 207. FIG. 21 is similar to FIG. 20, but shows solid drug pellets 25 within cavity 201. FIG. 22 shows (in an orientation that is inverted relative to FIG. 21) the terminal (or distal) end of tubing 197 and illustrates electrode tip 208 and fluid outlet 210. When opposite charges are applied to electrode 207 and wire tip 208, an electro-osmotic flow is induced to a natural low resistance outlet within a cochlea or other target tissue. Interstitial fluid enters cavity 201 through semi-permeable membrane 200. In other embodiments, a separate tube is used (instead of membrane 200) to withdraw fluid from another bodily region that is remote from the drug reservoir. Fluid entering cavity 201 dissolves drug in cavity 201 and delivers the drug to the target tissue.

Figure 23:
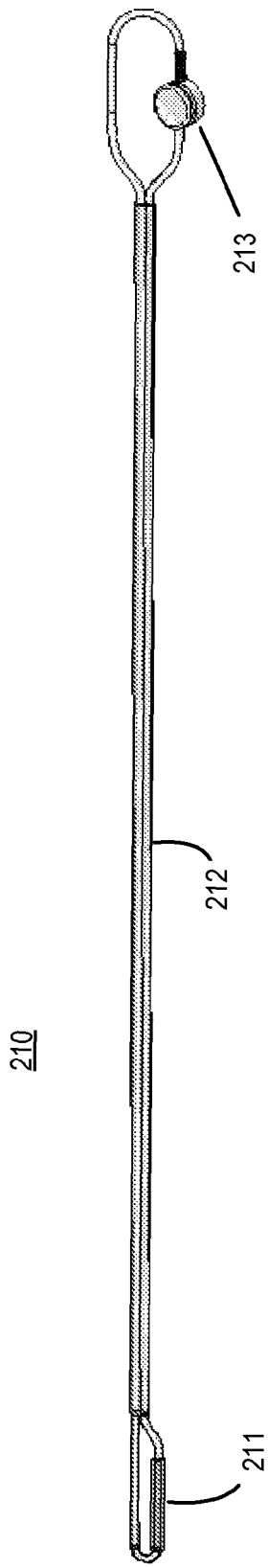
FIGS. 23 and 24 show an embodiment implementing magnetically-stimulated delivery of drug.
Figure 24:
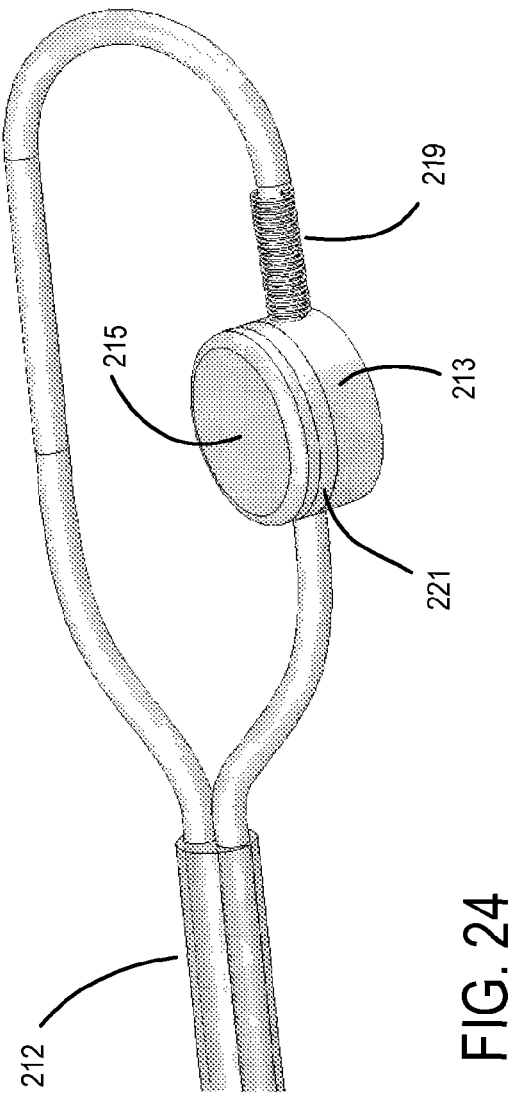
Figure 25:
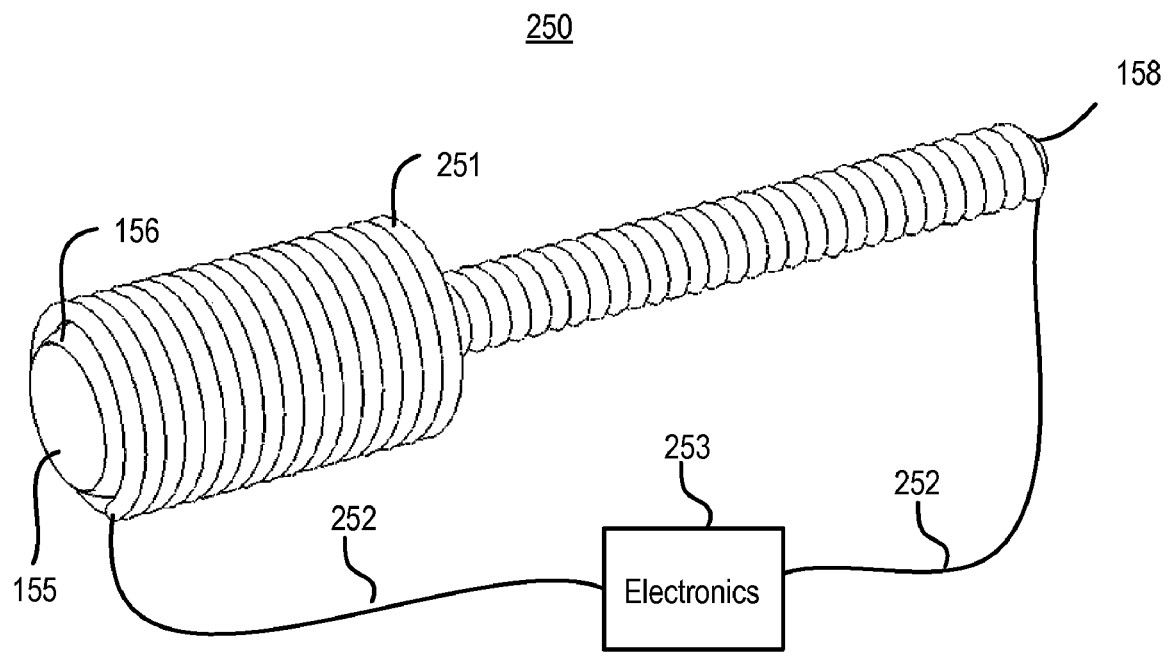
FIG. 25 is another embodiment implementing magnetically-stimulated delivery of drug.

Some embodiments include magnetic field induced delivery of drug. Two such embodiments are shown in FIGS. 23-25. Current applied through a coil surrounding a delivery catheter will produce a directional magnetic field. If there are magnetic or charged particles inside the catheter, they can be used to carry drug. For example, carrier nanoparticles formed from a magnetic material can be propelled by the magnetic field and circulated around a loop or expelled from another type of terminal component. In some embodiments (e.g., that of FIGS. 23 and 24), a hollow fiber wall allows dissolved drug to pass through but does not allow magnetic carrier particles to pass through. Thus, the magnetic carrier will load at the solid drug surface and release its load at the exit pore, such as the hollow fiber. The magnetic field will ensure there is a circular flow within the tubing.

FIG. 23 shows a system 210 configured to provide magnetic field induced drug delivery. A magnetic field actuator attached to a reservoir 213 induces a magnetic field so as to carry fluid and drug through a dual lumen catheter 212 to a hollow fiber loop 211. FIG. 24 is an enlarged view of a portion of system 210 and shows reservoir 213 with attached electronics package 221, battery 215 and magnetic coil 219. Magnetic coil 219 surrounds a tube (exiting reservoir 213) containing fluid, drug, and magnetic or charged particles, and creates a magnetic field that circulates the fluid around the system.

FIG. 25 shows a system 250 according to another embodiment providing magnetic field induced drug delivery. System 250 includes a system such as shown in FIG. 13, e.g., a reservoir 156 having a semi-permeable membrane 156 on one end and a catheter 158 for delivery of drug to a target region. In system 250, however, a coil 251 surrounds reservoir 156 and at least a portion of catheter 158. Electronics 253 provide electric current to coil 251 via wires 252, thereby creating a magnetic field to induce flow of charge drug particles (e.g., drug ions) from a drug chamber inside reservoir 156 and through catheter 158 to the target region. In some embodiments, semi-permeable membrane 155 is replaced with a one-way valve to admit fluid (e.g., physiological fluid from a bodily region in which reservoir 156 has been implanted) into the drug chamber. In some additional embodiments, electronics 253 are contained within the housing of reservoir 156. A 3-D antibacterial filter may also be included within catheter 158 or elsewhere in the system.

Embodiments of the invention can also be implemented using devices and methods described in U.S. patent application Ser. No. 11/337,815 (filed Jan. 24, 2006 and titled "Apparatus and Method for Delivering Therapeutic and/or Other Agents to the Inner Ear and to Other Tissues," published as U.S. Patent Application Publication No. 2006/0264897).

In some embodiments, an electronics package coupled to a drug reservoir (e.g., electronics package 203 in FIG. 20 or electronics package 221 in FIG. 24) includes components for sensing properties of a drug/vehicle solution (or suspension). The sensed properties could include one or more of pH, absorbance of light, electrical conductivity, light scattering, drug or electrolyte concentrations, etc. These sensed properties can then be used, via appropriate electronics, to adjust operation of a pump (internal or external) or other elements (e.g., magnetic coil or electrophoretic electrodes). An electronics package could also (or alternatively) be configured to detect sound or other physical parameters (e.g., tissue electrical activity) and/or be in communication with remote sensors.

In at least some additional embodiments, a vehicle used to remove drug from one or more solid drug masses in a reservoir may itself be a pre-mixed suspension of nanoparticles containing a drug (or drugs). In still other embodiments, drug devices according to various embodiments can be used to deliver a pre-mixed suspension of nanoparticles containing a drug (or drugs) without employing a solid drug mass in a reservoir chamber. In either case, the nanoparticles can be drug nanoparticles or nanoparticles of a carrier material to which drug has been absorbed/adsorbed or otherwise attached.

As previously indicated, devices and methods such as are described herein can be used to provide sustained, long term delivery of a drug. Such devices and methods can also be used to provide intermittent drug delivery on a long term basis. For example, a reservoir holding a solid drug mass could be implanted in a patient's body. That reservoir can then be periodically connected (e.g., using a subcutaneous port in fluid communication with the reservoir) to a source of vehicle.

Similar to system 10 shown in FIG. 1, the reservoirs shown in FIGS. 3A-3F, 5, 8 and 9 can be implanted in a human or other animal and coupled on one end (e.g., inlet 50 of reservoir 40, inlet barb 62 of reservoir 60) with a catheter to a vehicle source (e.g., an implanted osmotic pump, a port into which vehicle is introduced from an external source). The other end (e.g., outlet 48 of reservoir 40, barb 63 of reservoir 60) can be connected via another catheter to a terminal component (which may also be implanted in the patient).

All patents, patent applications, and references cited in this disclosure are expressly incorporated herein by reference. The following specific examples are provided for purposes of illustration only and are not intended to limit the scope of the invention.

EXAMPLE 1

Fabrication of Pellets of Gacyclidine Base

Water (500 mL) was brought to a boil. This hot water bath was then used to melt solid gacyclidine base. After placing 35 mg of gacyclidine base in a small glass vial, the vial was incubated in the hot water bath (90-100° C.) until the gacyclidine base melted. Small aliquots (2 µL) of the melted gacyclidine base were then transferred to polypropylene tubes (1.5 mL in size) and allowed to stand at room temperature until the gacyclidine base had solidified.

Solidification of the melted gacyclidine is typically complete within 30 minutes, but can occasionally take many hours. About half of the time, a single solid mass is obtained that slowly grows from a single focus. For those aliquots that result in multiple smaller crystalline/amorphous masses on standing, the tube containing the aliquot can be incubated in a hot water bath (90-100° C.) until it is melted a second time. Upon cooling, a second crop of single solid masses will be obtained. This process can be repeated, as necessary, until all aliquots of gacyclidine base have been converted to single solid masses.

Single solid masses (drug pellets) obtained in this way have an average weight of 1.5±0.3 mg and are hemispheres with a diameter of about 1.9 mm. These drug pellets have sufficient mechanical stability to be detached from the surface on which they are grown and transferred to a dissolution chamber. The shape of the solid pellet is determined by the shape of the container in which the liquid drug is solidified. By using containers having different shapes, drug can be solidified so as to conform to a shape of a drug reservoir in which the solid drug will be placed.

EXAMPLE 2

Dissolution of Gacyclidine Base in a Continuous Flow Reactor

A drug chamber similar to the one illustrated in FIGS. 2 and 4 was loaded with 11 pellets of gacyclidine base having a combined mass of 18 mg. This drug-loaded chamber was eluted at a flow rate of 20 µL/hr at room temperature (23±2° C.) using a MiniMed 508 syringe pump (available from Medtronics MiniMed of Northridge, Calif.). The syringe was loaded with 3 mL of Ringer's solution containing 0.05 to 3 mM hydrochloric acid. The eluted volume was collected in PTFE tubing attached to the pump drug capsule assembly, after a 3-D antibacterial filter. The pH of this solution was determined by use of a pH meter equipped with a Calomel electrode. Drug concentration was determined by HPLC.

Figure 26:
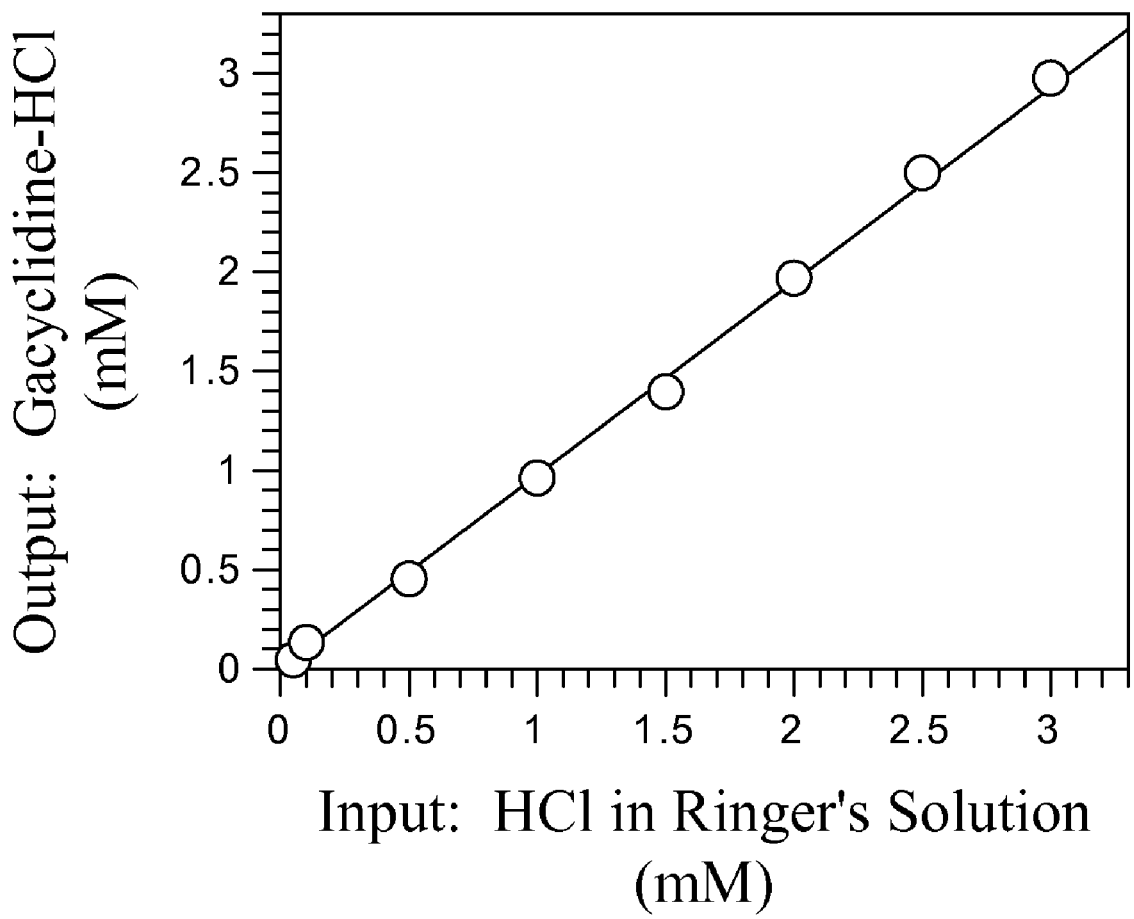
FIG. 26 shows the elution of gacyclidine from a drug dissolution chamber as a function of the concentration of hydrochloric acid in Ringer's solution used to erode pellets of crystalline gacyclidine base.

The highest pH of the eluted drug solution (5.9) was obtained at 0.05 mM hydrochloric acid, and the lowest pH of the eluted drug solution (5.6) was obtained at 3 mM hydrochloric acid. These pH values indicate quantitative conversion of the hydrochloric acid to the drug salt and are consistent with the pH expected for solutions of the hydrochloride salt. As shown in FIG. 26, the concentration of gacyclidine obtained in the output from the continuous flow reactor was linearly correlated with the concentration of hydrochloric acid used to elute the chamber. These data had a correlation of 0.976±0.049 in gacyclidine concentration per hydrochloric acid concentration used for elution and an intercept at zero concentration of hydrochloric acid of 0.0014±0.0061 mM gacyclidine.

Numerous characteristics, advantages and embodiments of the invention have been described in detail in the foregoing description with reference to the accompanying drawings. However, the above description and drawings are illustrative only. The invention is not limited to the illustrated embodiments, and all embodiments of the invention need not necessarily achieve all of the advantages or purposes, or possess all characteristics, identified herein. Various changes and modifications may be effected by one skilled in the art without departing from the scope or spirit of the invention. Although example materials and dimensions have been provided, the invention is not limited to such materials or dimensions unless specifically required by the language of a claim. The elements and uses of the above-described embodiments can be rearranged and combined in manners other than specifically described above, with any and all permutations within the scope of the invention. As used herein (including the claims), "in fluid communication" means that fluid can flow from one component to another; such flow may be by way of one or more intermediate (and not specifically mentioned) other components; and such may or may not be selectively interrupted (e.g., with a valve). As also used herein (including the claims), "coupled" includes two components that are attached (movably or fixedly) by one or more intermediate components.

We claim:

1. An apparatus, comprising:
a drug reservoir configured for implantation in the body cavity of a living human and having a drug reservoir cavity, the drug reservoir cavity containing solid basic form gacyclidine not bound to a biodegradable polymer, the drug reservoir cavity configured to receive a substantially continuous flow of a fluid having an acid concentration corresponding to a desired gacyclidine dosage, the drug reservoir cavity further configured to output the substantially continuous flow of fluid entraining gacyclidine in the desired dosage;
a catheter configured for implantation into the body cavity of a living human with the drug reservoir, the catheter including a lumen forming a conduit for the substantially continuous flow of fluid entraining gacyclidine in the desired dosage; and
a terminal component coupled to the catheter and including at least one outlet in fluid communication with the catheter lumen, at least a portion of the terminal component including the outlet being configured for direct implantation into the inner ear tissue of a living human into the body cavity of which the drug reservoir and catheter have been implanted, and wherein
the apparatus is configured to change the acid concentration, after initial placement of gacyclidine in the drug reservoir, without removal of gacyclidine from the drug reservoir, and without removal of the apparatus from the body cavity of the living human.

2. The apparatus of claim 1, wherein the terminal component comprises a cochlear implant electrode.

3. The apparatus of claim 1, further comprising a screen located in the drug reservoir cavity and positioned to prevent migration of the solid basic form gacyclidine from the drug reservoir cavity.

4. The apparatus of claim 1, further comprising a pump configured for implantation into the body cavity of a living human with the drug reservoir and configured to propel the fluid past the solid basic form gacyclidine in the drug reservoir cavity.

5. The apparatus of claim 4, wherein the pump is external to a housing for the drug reservoir.

6. The apparatus of claim 4, wherein the pump and the drug reservoir are contained within the same housing.

7. The apparatus of claim 1, wherein the drug reservoir is configured for non-destructive opening and fluid-tight reclosure so as to permit replenishment of the solid basic form gacyclidine.

8. The apparatus of claim 1, comprising an electronics package and one or more electrodes configured to provide electrical stimulation to the middle or inner ear tissue.

9. The apparatus of claim 1, further comprising an electronics package and one or more magnetic coils configured to produce a magnetic field so as to propel particles in the fluid that has flowed past the solid basic form gacyclidine.

10. The apparatus of claim 9, wherein the particles are magnetic nanoparticles.

11. The apparatus of claim 1, wherein the catheter comprises at least two fluid conduits, each of the fluid conduits having a first opening in fluid communication with the drug reservoir cavity and a second opening positionable remotely from the drug reservoir cavity, wherein the apparatus is configured to expel the fluid and entrained gacyclidine from one of the second openings and to receive the fluid through the other of said second openings.

12. The apparatus of claim 1, further including a subcutaneously implantable port.

13. The apparatus of claim 12, wherein the drug reservoir is part of the subcutaneously implantable port.

14. The apparatus of claim 1, wherein the drug reservoir includes a semi-permeable membrane or one-way valve positioned to admit physiological fluid into the drug reservoir cavity.

15. The apparatus of claim 1, further comprising an electronics package and one or more sensors configured to sense, as to vehicle and entrained drug from the solid basic form gacyclidine, one or more of the following:
pH, absorbance of light, electrical conductivity, light scattering, drug concentration and electrolyte concentration.

16. The apparatus of claim 1, further comprising an electronics package and one or more sensors configured to sense sound.

17. The apparatus of claim 1, further comprising an electronics package and one or more sensors configured to sense tissue electrical activity.

18. The apparatus of claim 1, further comprising a supply of a liquid vehicle, and wherein the apparatus is configured to utilize the liquid vehicle as the fluid.

19. The apparatus of claim 1, wherein the terminal component comprises a needle configured for passage through bone.

20. The apparatus of claim 1, wherein the solid basic form gacyclidine is unencapsulated and lacks a binder.

* * * * *